(12) United States Patent
Murray et al.

(10) Patent No.: US 7,199,255 B2
(45) Date of Patent: *Apr. 3, 2007

(54) IMINO-AMIDE CATALYSTS FOR OLEFIN POLYMERIZATION

(75) Inventors: Rex Eugene Murray, Cross Lanes, WV (US); Arnold M. Harrison, South Charleston, WV (US)

(73) Assignee: Univation Technologies, LLC, Houston, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 10/923,597

(22) Filed: Aug. 20, 2004

(65) Prior Publication Data

US 2005/0187362 A1  Aug. 25, 2005

Related U.S. Application Data

(63) Continuation-in-part of application No. 10/023,255, filed on Dec. 18, 2001, now Pat. No. 6,919,467, and a continuation-in-part of application No. 10/023,256, filed on Dec. 18, 2001, now Pat. No. 6,864,205.

(51) Int. Cl.
*C07F 9/30* (2006.01)
*C07F 7/08* (2006.01)
*C07F 15/06* (2006.01)
*C07F 7/00* (2006.01)
*B01J 31/00* (2006.01)

(52) U.S. Cl. .................. 556/20; 556/12; 556/32; 556/51; 502/167

(58) Field of Classification Search .............. 556/1, 556/12, 20, 28, 32, 42, 45, 51, 57, 117, 136, 556/146; 534/15; 502/167

See application file for complete search history.

(56) References Cited

U.S. PATENT DOCUMENTS

| | | | |
|---|---|---|---|
| 5,707,913 A | 1/1998 | Schlund et al. |
| 6,096,676 A | 8/2000 | Murray |
| 6,174,975 B1 | 1/2001 | Johnson et al. |
| 6,197,714 B1 | 3/2001 | Bansleben et al. |
| 6,262,198 B1 | 7/2001 | Schlund et al. |
| 6,265,505 B1 | 7/2001 | McConville et al. |
| 6,268,448 B1 | 7/2001 | Collins et al. |
| 6,271,323 B1 | 8/2001 | Loveday et al. |
| 6,274,684 B1 | 8/2001 | Loveday et al. |
| 6,281,306 B1 | 8/2001 | Oskam et al. |
| 6,300,438 B1 | 10/2001 | McConville |
| 6,320,002 B1 | 11/2001 | Murray et al. |
| 6,320,005 B1 | 11/2001 | Murray |
| 6,380,328 B1 | 4/2002 | McConville et al. |
| 6,399,722 B1 | 6/2002 | Szui et al. |
| 6,399,724 B1 | 6/2002 | Matsui et al. |
| 6,410,660 B1 | 6/2002 | Johnson et al. |
| 6,410,664 B1 | 6/2002 | Bansleben et al. |
| 6,417,304 B1 | 7/2002 | McConville et al. |
| 6,458,738 B1 | 10/2002 | Cook |
| 6,472,342 B2 | 10/2002 | Agapiou et al. |
| 6,475,946 B1 | 11/2002 | Rix |
| 6,479,422 B1 | 11/2002 | Eilerts |
| 6,482,903 B1 | 11/2002 | Agapiou et al. |
| 6,489,414 B1 | 12/2002 | Schuchardt |
| 6,489,497 B1 | 12/2002 | Brookhart et al. |
| 6,511,936 B1 | 1/2003 | Theopold et al. |
| 6,518,444 B1 | 2/2003 | McConville et al. |
| 6,521,561 B1 | 2/2003 | Jacobsen et al. |
| 6,544,919 B1 | 4/2003 | Tagge et al. |
| 6,559,091 B1 | 5/2003 | Moody et al. |
| 6,579,823 B2 | 6/2003 | Moody et al. |
| 6,579,998 B2 | 6/2003 | Sita et al. |
| 6,586,358 B2 | 7/2003 | Llatas et al. |
| 6,593,266 B1 | 7/2003 | Matsui et al. |
| 6,610,627 B2 | 8/2003 | Murray |

(Continued)

FOREIGN PATENT DOCUMENTS

DE 4202889 8/1993

(Continued)

OTHER PUBLICATIONS

Cotton et al, "Advanced Inorganic Chemistry A Comprehensive Text," John Wiley & Sons, 776-778, 790, 792-793 (1980).

(Continued)

*Primary Examiner*—J. A. Lorengo
*Assistant Examiner*—J. Pasterczyk
(74) *Attorney, Agent, or Firm*—Kevin M. Faulkner; Leandro Arechederra

(57) ABSTRACT

The present invention provides a catalyst precursor, a catalyst system comprising the precursor, and a polymerization method using the catalyst system, an embodiment of the precursor is selected from the following structures:

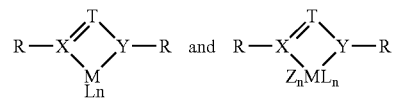

wherein T is a bridging group; M is selected from Groups 3 to 13 atoms, and the Lanthanide series of atoms the Periodic Table of the Elements; Z is a coordination ligand; each L is a monovalent, bivalent, or trivalent anionic ligand; X and Y are each independently selected from nitrogen, oxygen, sulfur, and phosphorus; each R can be the same or different and is a bulky substituent that is sterically hindering with respect to X and Y.

17 Claims, No Drawings

U.S. PATENT DOCUMENTS

| | | | |
|---|---|---|---|
| 6,632,769 B2 | 10/2003 | Wenzel et al. | |
| 6,632,770 B2 | 10/2003 | Holtcamp | |
| 6,660,677 B1 | 12/2003 | Mackenzie et al. | |
| 6,660,679 B2 | 12/2003 | Holtcamp et al. | |
| 6,660,815 B2 | 12/2003 | Agapiou et al. | |
| 6,670,297 B1 | 12/2003 | Brookhart et al. | |
| 6,686,491 B2 | 2/2004 | Cavell et al. | |
| 6,831,187 B2* | 12/2004 | Murray | 556/51 |
| 6,864,205 B2* | 3/2005 | Murray | 502/103 |
| 6,919,467 B2* | 7/2005 | Murray | 556/12 |
| 2002/0120081 A1 | 8/2002 | Guan | |
| 2003/0153697 A1 | 8/2003 | Boussie et al. | |
| 2005/0003075 A1* | 1/2005 | Bradley et al. | 427/96.8 |
| 2005/0159303 A1* | 7/2005 | Boussie et al. | 502/155 |
| 2005/0288505 A1* | 12/2005 | Liang | 546/2 |
| 2006/0094591 A1* | 5/2006 | Gibson et al. | 502/150 |

FOREIGN PATENT DOCUMENTS

| | | |
|---|---|---|
| EP | 0320169 | 6/1989 |
| EP | 0509233 | 10/1992 |
| EP | 0349886 | 9/1995 |
| EP | 0761694 | 3/1997 |
| EP | 0803520 | 10/1997 |
| EP | 0950667 | 10/1999 |
| JP | 2000128922 | 10/1998 |
| JP | 2000-128922 | 5/2000 |
| WO | WO-9212162 | 7/1992 |
| WO | WO-9533497 | 12/1995 |
| WO | WO-9623010 | 8/1996 |
| WO | WO-9633202 | 10/1996 |
| WO | WO-9702298 | 1/1997 |
| WO | WO-9745434 | 12/1997 |
| WO | WO-0246246 | 6/2002 |

OTHER PUBLICATIONS

Gibson et al, "Synthesis and structural characterization of aluminum imino-amide and pyridyl-amide complexes: bulky monoanionic N,N chelate ligands via methyl group transfer," Journal of Organometallic Chemistry 550, 453-456, 1998.

Fuhrmann et al, "Octahedral Group 4 Metal Complexes that contain Amine, Amido and Aminopyridinato Ligands: Synthesis, Structure, and Application in a-Olefin Oligo- and Polymerization," Inorg. Chem 35, Feb. 1996, pp. 6742-6745.

Briotovsek et al, "Novel Olefin Polymerization Catalysts Based on Iron and Cobalt," Chem Commun. May 1998, pp. 849-850.

Deelman et al, "Lithium Derivatives of Novel Monoaniomic Di-N-N- chelating Pyridyl- and Quinolyl-I-azaallyl Ligands," Organometalics 16, Aug. 1997, pp. 1247-1252.

Deelman et al, "Novel monanionic di-N-N- centered chealting ligands and the C1 and C2 symmetrical zirconium complexes," Jurnal of Organomettalic Chemistry 513, Nov. 1996, pp. 281-285.

Hitchcock et al, "Transformation of the Bis(trimethylsily) methyl into Aza-allyl and B-Diketinimato Ligands: the X-Ray Structures of [li{N(R)C(Bu1)CH(R)}]2 and [Zr{N(R)C(Bu1)CHC(Ph)N(R)}Cl3] (R=SiMe3)" J. Chem. Soc., Chem Comm. Aug. 1994, pp. 2637-2638.

Hitchcock et al, "Transformation of the Bis(trimethylsily)methyl into a B-Diketinimato Ligand: the X-Ray Structure of [Li(IL'L')]2 SNCi(Me)2 (L'L') amd SnCi(Me)2(LL), (L'L') (L'L'= N(R)C(Ph)NRLL=N)H)C(Ph)NH, R—SiMe3)" J. Chem. Soc., Chem Commun. May 1994, pp. 1699-1700.

Clarke et al, "Structural Investigations of the Dipyrromethene Complexes of Calcium(II), Nickel(II) and Copper(II)," Inorganica Chimica Acta. 166, Jun. 1989, pp. 221-231.

Tjaden et al, "Synthesis, Structures, and Reactivity of (R6-acen)ZRR2 and (R6-acenZR(R') Complexes (R=H, F: R'=CH2Cme3, CH2PH)," Organometallics 14, Jul. 1995, pp. 371-386.

Corazza et al, cis and trans Dichloro-derivatives of Six and Seven co ordinate Zirconium and Hafnium bonded to Quadridentate Schiff-base Ligands. Crystal Structures of [Zr(acen)Cl2(thf)], [M(salphen)Cl2(thf)] 0.5thf, [M9acen)Cl2. (M=Zr of Hf), and [Zr(msal)Ci2] acen=N,N'=ethylenebis (acetylacetoneiminate), salphen=N,N'-o-phenylenebis (salicylideneiminate), msal=N-methylsalicylideneiminate, and thf=tetrahydrofuran] J. Chem. Soc. Dalton Trans. Aug. 1990, pp. 1335-1344.

Cozzi et al, "Oxazoline Early Transition Metal Complexes: Functionalizable Achiral Titanium(IV), Titanium (III), Zirconium(IV), Vanadium(III), and Cj=hiral Zirconium(IV) Bls(oxazoline) complexes" Inorg. Chem 34, Dec. 1995, pp. 2921-2930.

Korine et al, "Bis(Trimethylsily)benzamidinate zirconium dichlorides. Active catalysts for ethlene polymerization." Journal of Organometallic Chemistry 503, Mar. 1995, pp. 307-314.

Gomez et al, "Mono-n-cyclopendtadienyl-benzamidinato chloro compounds of titanium, zirconium and hafnium," Journal of Organmetallic Chemistry 491, Aug. 1995, pp. 153-158.

Flores et al, "[N,N-Bis(trimethylsily)benzamidinato]titanium and zirconium Compounds. Synthesis and Application as Persursors for the Syndiospecific Polymerization of Styrene," Organomettalics 14, Oct. 1995, pp. 1827-1833.

Dias et al, "N-Methyl-29methylamino)troponiminate Complexes of Tin(II), Gallium(III), and Indium(III), Synthesis of [(ME)2ATI]2Gal and {(Me)2ATI 2InCl Using the Tin(III) Reagent [(Me02ATI]2SN," Inorg. Chem. 35, Jun. 1996, pp. 6546-6551.

Cotton et al, "Structural Studies of formamidine compounds: from neutral to anionic and cationic species," Polyheron vol. 16, No. 3, Apr. 1997, pp. 541-550.

Gornitzka et al., "Coordinationo of the Bis(pyridyl)methyl Substiuent to Group 1 and 13 Metals," Organmetallics 13, May 1994, pp. 4398-4405.

Roesky et al, "Benzamidnatokomplexe mit Haupt- and Nebengruppen-Elementen—Strukturen von PhC(NSiMe3)2TiCl2 and PhC(NSiMe3)2MoO2," Chem Ber. 121, Feb. 1988, pp. 1403-1406.

Cloke et al, "Zirconium Complexes incorporating the New Tridentate Diamide Ligand [(Me3Si)N{CH2CH2N(SiMe3)}2]2 (L); the Crystal Structure of [Zr(BH4)2L] and ZrCl{CH(SiMe3)2}L)" J. Chem Soc. Dalton Trans, Jul. 1995, pp. 25-30.

Linden et al., "Polymerization of a-Olefins and Butadiene and Catalytic Cyclotrimerization of 1-Alkynes by a New Class of Group IV Catalysts. Control of Molecular Weight and Polymer Microstructure via Ligand Turning in Sterically Hindered Chelating Phenoxide Titanium and Zirconium Species," J. Am. Chem Soc. 117, Jul. 1995, pp. 3008-3021.

Brand et al, "Facile Reduction of a DialkylZirconium(IV) Octaethylporphyrin (OEP) Complex by H2 Crystal Structure and Spectroscopic Characterization of [(OEP)ZrCH2SIMe3]" Agnew Chem Int. Ed. Engl. 33 No. 1, Jul. 1994, pp. 95-97.

Solari et al, "Functionalizedable 5,5,10,10,15,15,20,20-Octaethylporphyrinogen Complexes of Early Transition Metals: Synthesis and Crystal Structure of Titanium-, Vanadium- and Chromium (III) Derivatives and a Two-electron Oxidation of the Porphyrinogen Skeleton," J. Chem Soc. Dalton Trans. Apr. 1994, pp. 2015-2017.

Uhrhammer et al, "Catioic d Metal Alkyls Incorporating Tetraaza Macrocycle Ancillary Ligands Synthesis and Reactivity of (Me8taa)M(R)+ and (Me4taen)M(R)+(M=Zr, Hf) Complexes" J. Am. Chem Soc. 115, Apr. 1993, pp. 8493-8494.

Giannini et al, "Tetraaza [14] annulenezirconium (iv) Complexes with Butadiene Ligands and their Relationship with Bis(cyclopentadienyl)zirconium(IV) Complexes," Angew Chem. Int. Ed. Engl. 33 No. 21, May 1994.

Kol et al, "Synthesis of Molybdenum and Tungsten Complexes that Contain Triamidoamine Ligands of the Type (C6F5NCH2CH2)3N and Activation of Dinitrogen by Molybdenum," J. Am. Chem.Soc. 116, Oct. 1994, pp. 4382-4390.

Bei et al, "Synthesis, Structure, Bonding and Ethylene Reactivity of Group 4 Metal Alkyl Complexes Incorporating 8-Quinolinolato Ligands," Organmetallics 16, Mar. 1997, pp. 3282-3302.

Tsukahara et al, "Neutral and Cationic Zirconium Benzyl Complexes Containing Bidentate Pyridine-Alkoxide Ligands. Synthesis and Olefin Polymerization Chemistry of (pyCR2O)2Zr(CH2Ph)2 and (pyCR2O)2Zr(CH2Ph) Complexes" Organometallics 16, Mar. 1997, pp. 3303-3313.

Kim et al, "Synthesis, Stryuctures, Dynamics and Oelfin Polymerization Behavior of Group 4 Metal (pyCAr2O)2M(NR2)2 Complexes Containing Bidentate Pyridine-Alkoxide Ancillary Ligands," Organmetallics 16, Mar. 1997, pp. 3314-3323.

Durfee et al, "Formation and Characterization of n-Imine and n-Azobenzene Derivavtives of Titanium Containing Ancillary Aryloxide Ligation," Organometallics vol. 9, Jan. 1990, pp. 75-80.

Lappert et al, "Recent Studies on metal and metalloid bid(trimethylsilyl) methyls and the transformation of the bis(trimethylsilyl)methyl into the azaallyl and B-diketinimato ligands," Journal of Organometallic Chemistry 500, Sep. 1995, pp. 203-217.

Fritsky etal, "Template synthesis of square-planar nickel (II) and copper comlexes based on hydrazide ligands," J. Chem. Soc., Dalton trans., 1998, pp. 3269-3274.

van den Beuken et al, "Oligomerisation of etherne by new palladium iminophosphine catalysts," Chem. Commun, 1998, pp. 223-224.

Myachina et al, "Coordination Compounds of Nickel (II) with N-(3-Hydroximino-2-Methylbutyl-2) methylamine," Russian Journal of Coordination Chemistry, vol. 26 No. 8, 2000, pp. 568-575.

Daugulis et al, "Polymerization of Ethylene with Cationic Palladium and Nickel Catalysts Containing Bulky Nonenolizable Imine-Phosphine Ligands," Organometallics 21, 2002, pp. 5926-5934.

* cited by examiner

IMINO-AMIDE CATALYSTS FOR OLEFIN POLYMERIZATION

RELATED APPLICATIONS

This application is a continuation-in-part of, and claims priority to, U.S. application Ser. No. 10/023,255, filed on Dec. 18, 2001, now U.S. Pat. No. 6,919,467 and to application Ser. No. 10/023,256, filed on Dec. 18, 2001 now U.S. Pat. No. 6,864,205.

FIELD OF THE INVENTION

The present invention relates to a family of novel imino-amide catalyst precursors and catalysts useful for the polymerization of olefins, such as ethylene, higher alpha-olefins, dienes, and mixtures thereof.

BACKGROUND OF THE INVENTION

A variety of metallocenes and other single site-like catalysts have been developed to prepare olefin polymers. Metallocenes are organometallic coordination complexes containing one or more π-bonded moieties (i.e., cyclopentadienyl groups) in association with a metal atom. Catalyst compositions containing metallocenes and other single site-like catalysts are highly useful for the preparation of polyolefins, producing relatively homogeneous copolymers at excellent polymerization rates while allowing one to closely tailor the final properties of the polymer as desired.

Recently, work relating to certain nitrogen-containing, single site-like catalyst precursors has been published. For example, WO 96/23101 relates to di(imine) metal complexes that are transition metal complexes of bidentate ligands selected from the group consisting of:

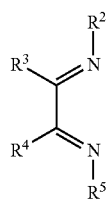
(V)

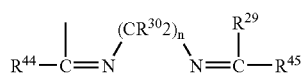
(VI)

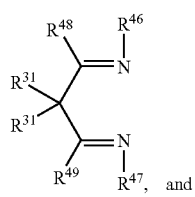
(VII)
and

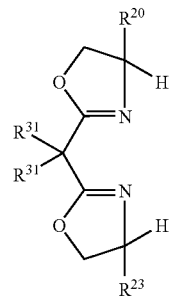
(VIII)

wherein said transition metal is selected from the group consisting of Ti, Zr, Sc, V, Cr, a rare earth metal, Fe, Co, Ni, and Pd;

$R^2$ and $R^5$ are each independently hydrocarbyl or substituted hydrocarbyl, provided that the carbon atom bound to the imino nitrogen atom has at least two carbon atoms bound to it;

$R^3$ and $R^4$ are each independently, hydrogen, hydrocarbyl, substituted hydrocarbyl, or $R^3$ and $R^4$ taken together are hydrocarbylene or substituted hydrocarbylene to form a carbocyclic ring;

$R^{44}$ is a hydrocarbyl or substituted hydrocarbyl, and $R^{28}$ is hydrogen, hydrocarbyl or substituted hydrocarbyl or $R^{44}$ and $R^{28}$ taken together form a ring;

$R^{45}$ is a hydrocarbyl or substituted hydrocarbyl, and $R^{29}$ is hydrogen, hydrocarbyl or substituted hydrocarbyl or $R^{45}$ and $R^{29}$ taken together form a ring;

each $R^{30}$ is independently hydrogen, hydrocarbyl or substituted hydrocarbyl, or two of $R^{30}$ taken together form a ring;

each $R^{31}$ is independently hydrogen, hydrocarbyl or substituted hydrocarbyl;

$R^{46}$ and $R^{47}$ are each independently hydrocarbyl or substituted hydrocarbyl, provided that the carbon atom bound to the imino nitrogen atom has at least two carbon atoms bound to it;

$R^{48}$ and $R^{49}$ are each independently hydrogen, hydrocarbyl, or substituted hydrocarbyl;

$R^{20}$ and $R^{23}$ are each independently hydrocarbyl, or substituted hydrocarbyl;

$R^{21}$ and $R^{22}$ are independently hydrogen, hydrocarbyl, or substituted hydrocarbyl; and n is 2 or 3;

and provided that:
the transition metal also has bonded to it a ligand that may be displaced by or added to the olefin monomer being polymerized; and
when the transition metal is Pd, said bidentate ligand is (V), (VII) or (VIII).

Also, U.S. Pat. No. 6,096,676 teaches a catalyst precursor having the formula:

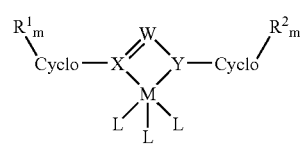

wherein M is a Group IVB metal;

each L is a monovalent, bivalent, or trivalent anion;

X and Y are each heteroatoms, such as nitrogen;

each Cyclo is a cyclic moiety;

each $R^1$ is a group containing 1 to 50 atoms selected from the group consisting of hydrogen and Group IIIA to Group VIIA elements, and two or more adjacent $R^1$ groups may be joined to form a cyclic moiety;

each $R^2$ is a group containing 1 to 50 atoms selected from the group consisting of hydrogen and Group IIIA to Group VIIA elements and two or more adjacent $R^2$ groups may be joined to form a cyclic moiety;

W is a bridging group; and each m is independently an integer from 0 to 5.

Also taught is a catalyst composition comprising this catalyst precursor and an activating co-catalyst, as well as a process for the polymerization of olefins using this catalyst composition.

Although there are a variety of single site catalysts taught in the art, some of which are commercially available, there still exist a need for improved catalysts and catalyst precursors that are capable of producing polyolefins having predetermined properties.

SUMMARY OF THE INVENTION

In one embodiment of the present invention, there is provided catalyst precursors of the formulae:

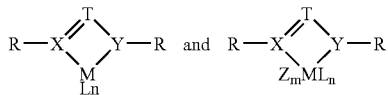

wherein T is a bridging group containing 2 or more bridging atoms;

M is a metallic element selected from Groups 3 to 13, and the Lanthanide series of the Periodic Table of the Elements;

Z is a coordination ligand;

each L is a monovalent, bivalent, or trivalent anionic ligand;

n is an integer from 1 to 6;

m is an integer from 1 to 3;

X is nitrogen or phosphorous;

Y is selected from the group consisting of nitrogen, oxygen, sulfur, and phosphorus; and, each R can be the same or different and is a bulky substituent with respect to X and Y and is selected from the group consisting of alkyl, alkenyl, cycloalkyl, heterocyclic (both heteroalkyl and heteroaryl), alkylaryl, arylalkyl, and polymeric groups. In one embodiment, T contains 2 or 3 bridging atoms and contains from 2 to 50 non-hydrogen atoms, at least one of which is a Group 14 atom. In another embodiment, T contains at least two primary alkyl groups on the atom adjacent to Y. In another embodiment, T contains a dimethyl group on the atom adjacent to Y.

In another embodiment of the catalyst precursor, T is selected from the group consisting of:

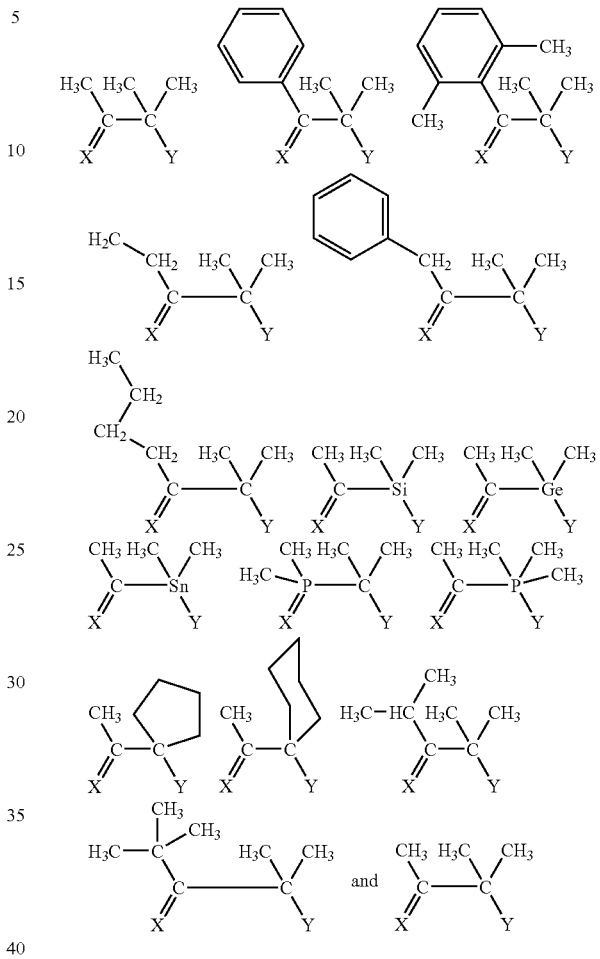

wherein X and Y are provided for convenience and are not part of the bridging group.

In another embodiment of the catalyst precursor, Z is selected from at least one of triphenylphosphine, a tris ($C_1$-$C_6$ alkyl)phosphine, a tricycloalkyl phosphine, a diphenyl alkyl phosphine, a dialkyl phenyl phosphine, a trialkylamine, an arylamine, a substituted or unsubstituted $C_2$ to $C_{20}$ alkene, an ester group, a $C_1$ to $C_4$ alkoxy group, an amine group, a carboxylic acid, a di($C_1$ to $C_3$) alkyl ether, an $\eta^4$-diene, tetrahydrofuran, and a nitrile. In yet another embodiment of the catalyst precursor, each L group contains from 1 to 50 non-hydrogen atoms and is selected from the group consisting of halogen containing groups, alkyl, aryl, alkenyl, alkylaryl, arylalkyl, hydrocarboxy, amides, phosphides, sulfides, silylalkyls, diketones, borohydrides, and carboxylates. In another embodiment of the catalyst precursor, L contains from 1 to 20 non-hydrogen atoms and selected from the group consisting of alkyl, arylalkyl, and halogen. In another embodiment of the catalyst precursor, n is an integer from 1 to 4. In another embodiment of the catalyst precursor, both X and Y are nitrogen. In another embodiment of the catalyst precursor, R contains from 3 to 50 non-hydrogen atoms and is selected from alkyl, alkenyl, cycloalkyl, heterocyclic, alkylaryl, arylalkyl, polymeric, and inorganic ring moieties. In another embodiment of the catalyst precursor, R contains from 4 to 20 non-hydrogen atoms. In another embodiment of the catalyst precursor, R has one or more of its carbon or hydrogen positions substituted with an element selected from Groups 14 to 17 of the Periodic Table of the Elements, other than carbon. In another embodiment of the catalyst precursor, R has one or more of its carbon or hydrogen positions substituted with an element selected from Groups 14 to 17 of the Periodic Table of the Elements, other than carbon.

In another embodiment of the catalyst precursor has the following formula:

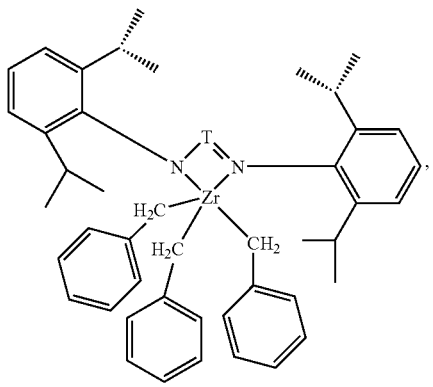

wherein T is a bridging group containing 2 or more bridging atoms.

In another embodiment, the catalyst precursor has a formula selected from the group consisting of:

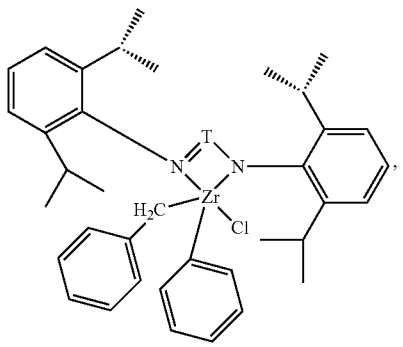

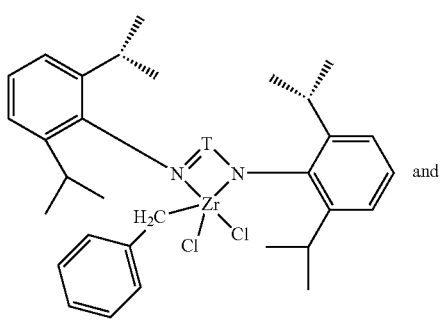

and

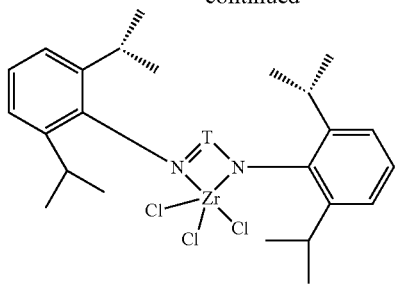

wherein T is a bridging group containing 2 or more bridging atoms.

In another embodiment of the catalyst precursor, M is selected from Groups 3 to 7 of the Periodic Table of Elements. In another embodiment of the catalyst precursor, each R group forms a substituted heterocyclic ring, said substituted heterocyclic ring including one of X and Y, or both X and Y, as a heteroatom. In another embodiment of the catalyst precursor, the substituted heterocyclic ring is 5-n-butyl pyridine. In another embodiment fo the catalyst precursor, the substituted heterocylic ring is 4-methyl pyridine.

In another embodiment, the catalyst precursor has the following structure:

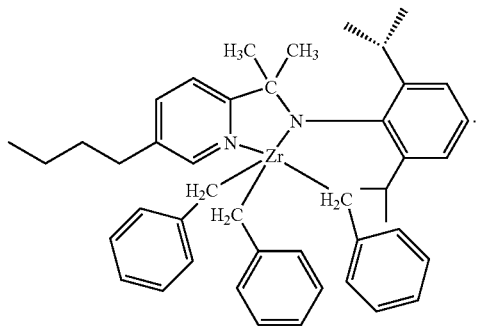

In another embodiment of the present invention, there is a catalyst composition comprising:
(a) a catalyst precursor compound represented by one or both of:

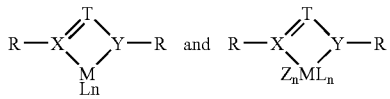

wherein T is a bridging group containing 2 or more bridging atoms;
M is an atom selected from Groups 3 to 13 atoms, and the Lanthanide series of atoms the Periodic Table of the Elements,
Z is a coordination ligand;
each L is a monovalent, bivalent, or trivalent anionic ligand;

n is an integer from 1 to 6;

m is an integer from 1 to 3;

X is nitrogen or phosphorous;

Y is selected from the group consisting of nitrogen, oxygen, sulfur, and phosphorus;

wherein each R can be the same or different and is a bulky substituent that is sterically hindering with respect to X and Y; and, (b) an activating cocatalyst.

In another embodiment of the catalyst composition, T contains 2 or 3 bridging atoms and contains from 2 to 50 non-hydrogen atoms, at least one of which is a Group 14 atom. In another embodiment, T contains at least two primary alkyl groups on the atom adjacent to Y. In another embodiment, T contains a dimethyl group on the atom adjacent to Y.

In another embodiment, of the catalyst composition, T is selected from the group consisting of:

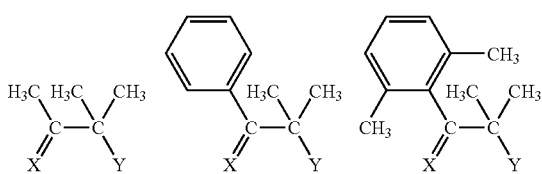

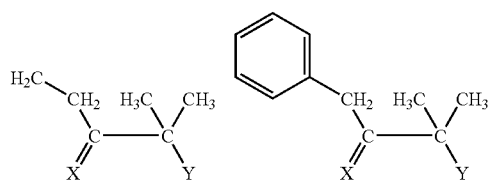

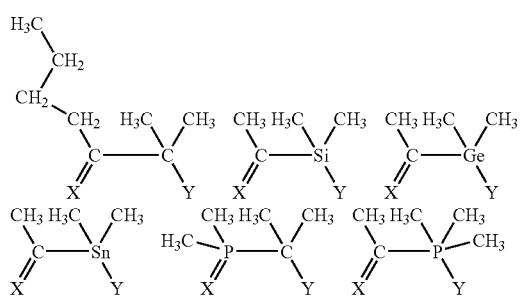

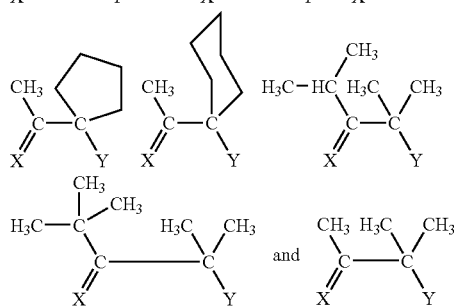

wherein X and Y are provided for convenience and are not part of the bridging group.

In another embodiment of the catalyst composition, Z is selected from at least one of triphenylphosphine, a tris ($C_1$–$C_6$ alkyl)phosphine, a tricycloalkyl phosphine, a diphenyl alkyl phosphine, a dialkyl phenyl phosphine, a trialkylamine, an arylamine, a substituted or unsubstituted $C_2$ to $C_{20}$ alkene, an ester group, a $C_1$ to $C_4$ alkoxy group, an amine group, carboxylic acid, a di($C_1$ to $C_3$)alkyl ether, an $\eta^4$-diene, tetrahydrofuran, and a nitrile.

In another embodiment of the catalyst composition, L contains from 1 to 50 non-hydrogen atoms and is selected from the group consisting of halogen containing groups, alkyl, aryl, alkenyl, alkylaryl, arylalkyl, hydrocarboxy, amides, phosphides, sulfides, silylalkyls, diketones, borohydrides, and carboxylates. In another embodiment of the catalyst composition, L contains 1 to 20 non-hydrogen atoms and is selected from the group consisting of alkyl, arylalkyl, and halogen. In another embodiment of the catalyst composition, n is an integer from 1 to 4. In another embodiment of the catalyst composition, both X and Y are nitrogen. In another embodiment of the catalyst composition, R contains from 3 to 50 non-hydrogen atoms and is selected from alkyl, alkenyl, cycloalkyl, heterocyclic, alkylaryl, arylalkyl, polymeric, and inorganic ring moieties. In another embodiment of the catalyst composition, R contains from 4 to 20 non-hydrogen atoms. In another embodiment of the catalyst composition, R has one or more of its carbon or hydrogen positions substituted with an element selected from Groups 14 to 17 of the Periodic Table of the Elements, other than carbon. In another embodiment, the catalyst composition has the following formula:

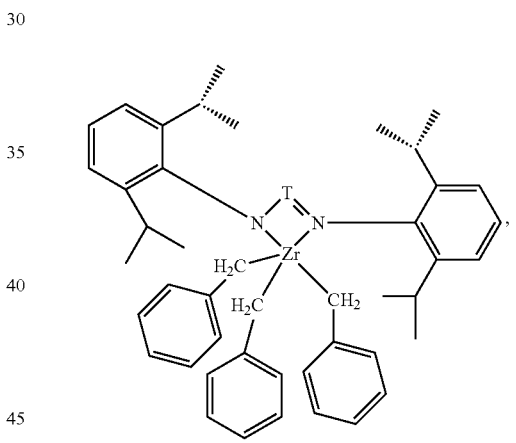

wherein T is a bridging group containing 2 or more bridging atoms.

In another embodiment, the catalyst composition has a following selected from the group consisting of:

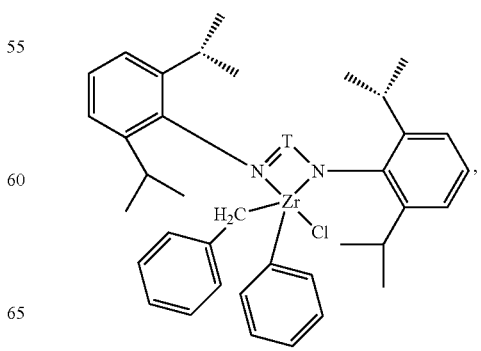

-continued

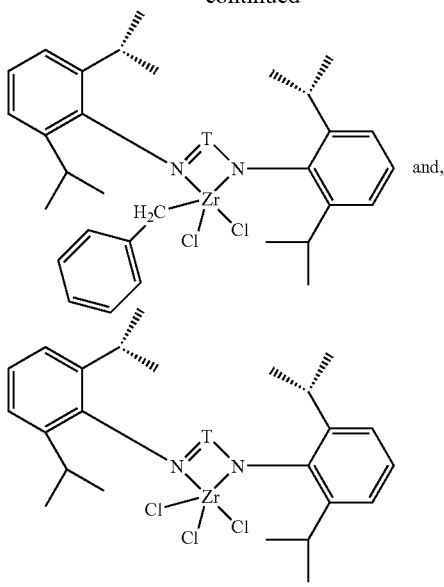
and, wherein T is a bridging group containing 2 or more bridging atoms.

In another embodiment of the catalyst composition, M is selected from Group Groups 3 to 7 of the Periodic Table of Elements. In another embodiment of the catalyst composition, R may form a ring with more than one bond to X and Y, and in some cases, includes at least one atom of T. In another embodiment of the catalyst composition, R forms a substituted heterocyclic ring, said substituted heterocyclic ring including one of X and Y, or both X and Y, as a heteroatom. In another embodiment of the catalyst composition, the substituted heterocylic ring is 5-n-butyl pyridine. In another embodiment of the catalyst precursor, the substituted heterocylic ring is 4-methyl pyridine.

In another embodiment, the catalyst precursor has the following structure:

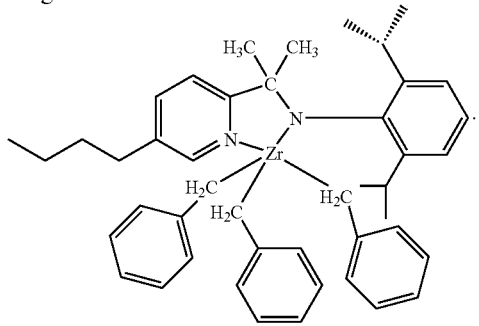

In another embodiment, the catalyst precursor has the following structure:

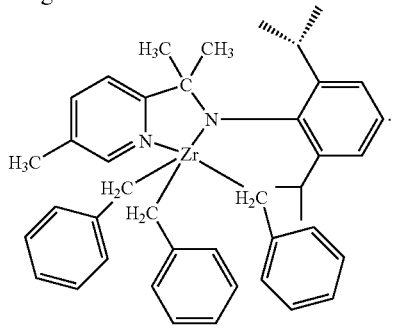

In another embodiment of the present invention, there is a method of polymerizing olefins comprising combining, under polymerization conditions, a catalyst precursor and an activating cocatalyst with one or more olefins selected from ethylene, propylene, 1-butene, 4-methyl-1-pentene, 1-pentene, 1-hexene, 1-octene, and 1-decene; the catalyst precursor represented by one or both of:

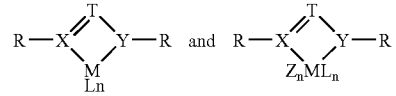

wherein T is a bridging group containing 2 or more bridging atoms;

M is an atom selected from Groups 3 to 13 atoms, and the Lanthanide series of atoms the Periodic Table of the Elements, Z is a coordination ligand;

each L is a monovalent, bivalent, or trivalent anionic ligand;

n is an integer from 1 to 6;

m is an integer from 1 to 3;

X is nitrogen or phosphorous;

Y is selected from the group consisting of nitrogen, oxygen, sulfur, and phosphorus;

wherein each R can be the same or different and is a bulky substituent that is sterically hindering with respect to X and Y.

In another embodiment of the method, T contains 2 or 3 bridging atoms and from 2 to 50 non-hydrogen atoms, at least one of which is a Group 14 atom. In another embodiment of the method, T contains at least two primary alkyl groups on the atom adjacent to Y. In another embodiment of the method, T contains a dimethyl group on the atom adjacent to Y. In another embodiment of the method, T is selected from the group consisting of:

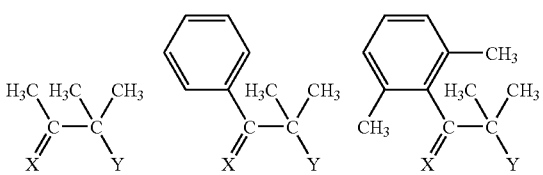

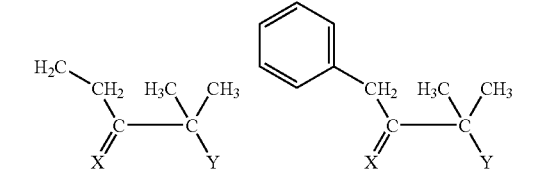

-continued

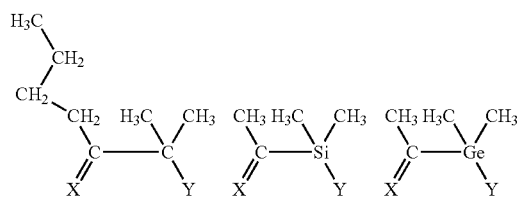

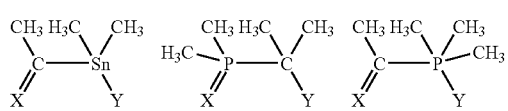

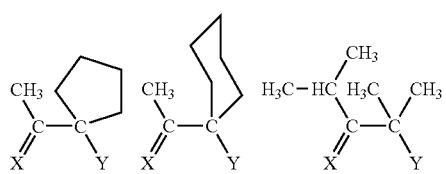

wherein X and Y are provided for convenience and are not part of the bridging group.

In another embodiment of the method, Z is selected from at least one of triphenylphosphine, a tris($C_1$–$C_6$ alkyl)phosphine, a tricycloalkyl phosphine, a diphenyl alkyl phosphine, a dialkyl phenyl phosphine, a trialkylamine, an arylamine, a substituted or unsubstituted $C_2$ to $C_{20}$ alkene, an ester group, a $C_1$ to $C_4$ alkoxy group, an amine group, carboxylic acid, a di($C_1$ to $C_3$) alkyl ether, an $\eta^4$-diene, tetrahydrofuran, and a nitrile. In another embodiment of the method, L is contains from 1 to 50 non-hydrogen atoms and is selected from the group consisting of halogen containing groups, alkyl, aryl, alkenyl, alkylaryl, arylalkyl, hydrocarboxy, amides, phosphides, sulfides, silylalkyls, diketones, borohydrides, and carboxylates. In another embodiment of the method, L contains 1 to 20 non-hydrogen atoms and is selected from the group consisting of alkyl, arylalkyl, and halogen. In another embodiment of the method, n is an integer from 1 to 4. In another embodiment of the method, both X and Y are nitrogen. In another embodiment of the method, R contains from 3 to 50 non-hydrogen atoms and is selected from alkyl, alkenyl, cycloalkyl, heterocyclic, alkylaryl, arylalkyl, polymeric, and inorganic ring moieties. In another embodiment of the method, R contains from 4 to 20 non-hydrogen atoms. In another embodiment of the method, R has one or more of its carbon or hydrogen positions substituted with an element selected from Groups 14 to 17 of the Periodic Table of the Elements, other than carbon. In another embodiment of the method, the catalyst precursor has the following formula:

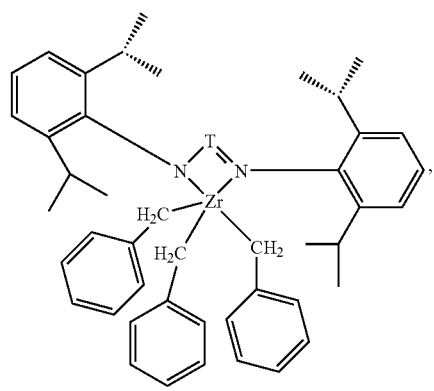

wherein T is a bridging group containing 2 or more bridging atoms.

In another embodiment of the method, the catalyst precursor is represented by a formula selected from the group consisting of:

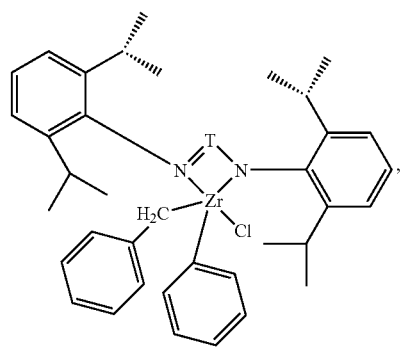

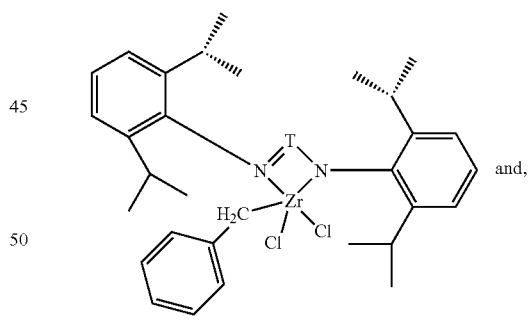

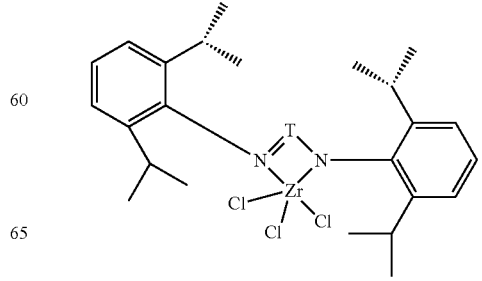

wherein T is a bridging group containing 2 or more bridging atoms.

In another embodiment of the method, M is selected from Group Groups 3 to 7 of the Periodic Table of Elements.

In another embodiment of the method, R may form a ring with more than one bond to X and Y. In another embodiment of the method, R forms a substituted heterocyclic ring, said substituted heterocyclic ring including one of X and Y, or both X and Y, as a heteroatom. In some embodiments of the method, the substituted heterocyclic ring is 5-n-butyl pyridine. In some embodiments of the method, the substituted heterocylic ring is 4-methyl pyridine.

In another embodiment of the method, the catalyst precursor has the following structure:

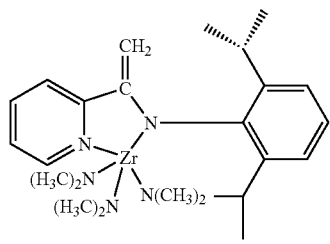

In another embodiment of the method, the catalyst precursor has the following structure:

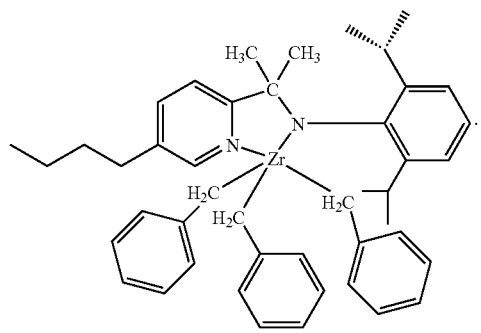

In another embodiment of the method, the catalyst precursor has the following structure:

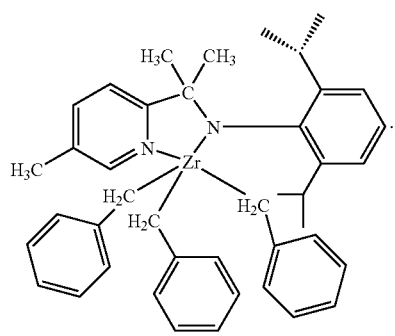

In another embodiment of the method, the polymerization is a gas phase polymerization process. In another embodiment of the method, the polymerization is a slurry phase polymerization process.

In another embodiment of the method, an activator is also combined under polymerization conditions. In another embodiment of the method, the one or more olefins comprises 1-hexene. In another embodiment of the method, the one or more olefins comprise ethylene and 1-hexene. In a specific embodiment, the a method produces isotactic poly-1-hexene.

DETAILED DESCRIPTION OF THE INVENTION

As used herein, the phrase "catalyst composition" includes at least one "catalyst precursor" and at least one "activator," both of which are described further herein. The catalyst composition may also include other components, such as supports, etc., and is not limited to the catalyst precursor and/or activator alone or in combination. The catalyst composition may include any number of catalyst components in any combination as described herein, as well as any activator in any combination as described herein.

As used herein, the phrase "catalyst precursor" includes any compound that, once appropriately activated, is capable of catalyzing the polymerization or oligomerization of olefins, the catalyst precursor comprising at least one Group 3 to Group 12 atom, and optionally at least one leaving group bound thereto.

As used herein, a "hydrocarbyl" includes aliphatic, cyclic, olefinic, acetylenic and aromatic radicals (i.e., hydrocarbon radicals) comprising hydrogen and carbon that are deficient by one hydrogen. A "hydrocarbylene" is deficient by two hydrogens.

As used herein, an "alkyl" includes linear, branched and cyclic paraffin radicals that are deficient by one hydrogen. Thus, for example, a —$CH_3$ group ("methyl") and a $CH_3CH_2$— group ("ethyl") are examples of alkyls.

As used herein, an "alkenyl" includes linear, branched and cyclic olefin radicals that are deficient by one hydrogen; alkynyl radicals include linear, branched and cyclic acetylene radicals deficient by one hydrogen radical.

As used herein, "aryl" groups includes phenyl, naphthyl, pyridyl and other radicals whose molecules have the ring structure characteristic of benzene, naphthylene, phenanthrene, anthracene, etc. For example, a $C_6H_5$— aromatic structure is an "phenyl", a $C_6H_4^{-2}$ aromatic structure is an "phenylene". An "arylalkyl" group is an alkyl group having an aryl group pendant therefrom, examples of which include benzyl, phenethyl, tolylmethyl and the like; an "alkylaryl" is an aryl group having one or more alkyl groups pendant therefrom, examples of which include tolyl, xylyl, mesityl, cumyl and the like.

As used herein, an "alkylene" includes linear, branched and cyclic hydrocarbon radicals deficient by two hydrogens. Thus, —$CH_2$— ("methylene") and —$CH_2CH_2$— ("ethylene") are examples of alkylene groups. Other groups deficient by two hydrogen radicals include "arylene" and "alkenylene".

As used herein, the phrase "heteroatom" includes any atom other than carbon and hydrogen that can be bound to carbon. A "heteroatom-containing group" is a hydrocarbon radical that contains a heteroatom and may contain one or more of the same or different heteroatoms. In one embodiment, a heteroatom-containing group is a hydrocarbyl group containing from 1 to 3 atoms selected from the group consisting of boron, aluminum, silicon, germanium, nitrogen, phosphorous, oxygen and sulfur. Non-limiting examples of heteroatom-containing groups include radicals of imines, amines, oxides, phosphines, ethers, ketones, oxoazolines heterocyclics, oxazolines, thioethers, and the like.

As used herein, "heterocyclic" refers to ring systems having a carbon backbone that comprise from 1 to 3 atoms selected from the group consisting of boron, aluminum, silicon, germanium, nitrogen, phosphorous, oxygen and sulfur, unless the heteroatom (non carbon atom) is described.

As used herein, an "alkylcarboxylate", "arylcarboxylate", and "alkylarylcarboxylate" is an alkyl, aryl, and alkylaryl, respectively, that possesses a carboxyl group in any position. Examples include $C_6H_5CH_2C(O)O$—, $CH_3(O)O$—, etc.

As used herein, the term "substituted" means that the group following that term possesses at least one moiety in place of one or more hydrogens in any position, the moieties selected from such groups as halogen radicals (esp., Cl, F, Br), hydroxyl groups, carbonyl groups, carboxyl groups, amine groups, phosphine groups, alkoxy groups, phenyl groups, naphthyl groups, $C_1$ to $C_{10}$ alkyl groups, $C_2$ to $C_{10}$ alkenyl groups, and combinations thereof. Examples of substituted alkyls and aryls includes, but are not limited to, acyl radicals, alkylamino radicals, alkoxy radicals, aryloxy radicals, alkylthio radicals, dialkylamino radicals, alkoxycarbonyl radicals, aryloxycarbonyl radicals, carbomoyl radicals, alkyl- and dialkyl-carbamoyl radicals, acyloxy radicals, acylamino radicals, arylamino radicals, and combinations thereof.

As used herein, structural formulas are employed as is commonly understood in the chemical arts; lines ("—") used to represent associations between a metal atom ("M") and a ligand, ligand atom or atom (e.g., cyclopentadienyl, nitrogen, oxygen, halogen ions, alkyl, etc.), as well as the phrases "associated with", "bonded to" and "bonding", are not limited to representing a certain type of chemical bond, as these lines and phrases are meant to represent a "chemical bond"; a "chemical bond" defined as an attractive force between atoms that is strong enough to permit the combined aggregate to function as a unit, or "compound".

A certain stereochemistry for a given structure or part of a structure should not be implied unless so stated for a given structure or apparent by use of commonly used bonding symbols such as by dashed lines and/or heavy lines.

Unless stated otherwise, no embodiment of the present invention is herein limited to the oxidation state of the metal atom "M" as defined below in the individual descriptions and examples that follow. The ligation of the metal atom "M" is such that the compounds described herein are neutral, unless otherwise indicated.

The catalyst precursors of the present invention will have the formula:

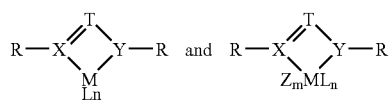

wherein T is a bridging group containing 2 or more bridging atoms, wherein at least one of the bridging atoms is a Group 14 element, preferably a carbon atom, and wherein T can also contain one or more elements selected from Groups 13 to 16 of the Periodic Table of the Elements. It is most preferred that all of the bridging atoms be carbon atoms. It is also preferred that there be only 2 or 3 bridging atoms. The total number of non-hydrogen atoms can be from 2 to 50, preferably from 2 to 20, and more preferably less than 10.

The most preferred T groups are those wherein there is a dimethyl grouping adjacent to Y.

Preferred bridging groups include, but are not limited to:

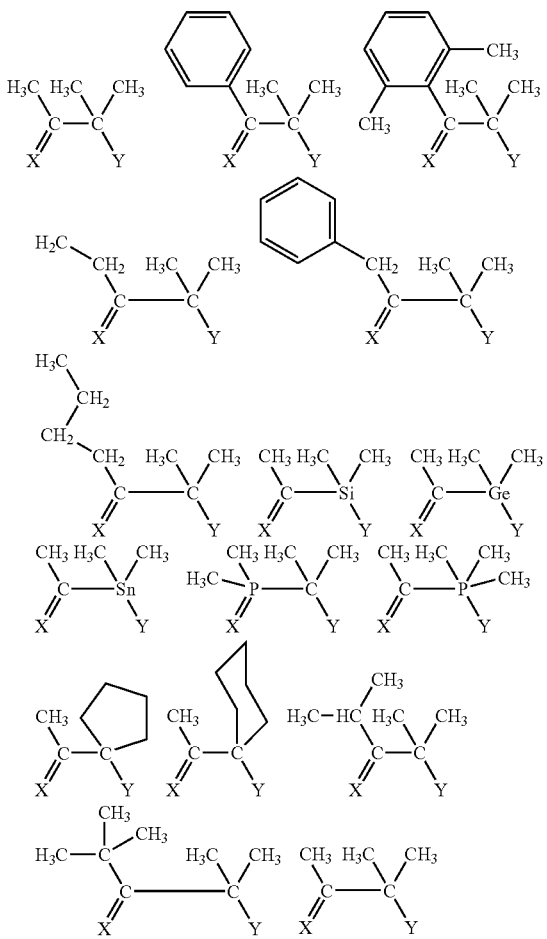

The X and Y substituents are included for convenience to show where the bridging groups would bridge.

M is a metallic element selected from Groups 1 to 15, preferably from Groups 3 to 13, more preferably from the transition metals of Groups 3 to 7, and the Lanthanide series of the Periodic Table of the Elements. The Periodic Table of the Elements referred to herein is that disclosed in LANGE'S HANDBOOK OF CHEMISTRY (McGraw Hill Handbooks, 15th ed. 1999).

Z is a coordination ligand. Preferred coordination ligands include triphenylphosphine, tris($C_1$–$C_6$ alkyl)phosphine, tricycloalkyl phosphine, diphenyl alkyl phosphine, dialkyl phenyl phosphine, trialkylamine, arylamine such as pyridine, a substituted or unsubstituted $C_2$ to $C_{20}$ alkene (e.g. ethylene, propylene, butene, hexene, octane, decene, dodecene, allyl, and the like) in which the substituent is a halogen atom (preferably chloro), an ester group, a $C_1$ to $C_4$ alkoxy group, an amine group (—$NR_2$ where each R individually is a $C_1$ to $C_3$ alkyl), carboxylic acid, di($C_1$ to $C_4$)alkyl ether, tetrahydrofuran (THF), a nitrile such a acetonitrile, an $\eta^4$-diene, and the like.

m is an integer from 1 to 3.

Each L is a monovalent, bivalent, or trivalent anionic ligand, preferably containing from 1 to 50 non-hydrogen atoms, more preferably from 1 to 20 non-hydrogen atoms and is independently selected from the group consisting of halogen containing groups; alkyl; aryl; alkenyl; alkylaryl; arylalkyl; hydrocarboxy; amides, phosphides; sulfides; silylalkyls; diketones; borohydrides; and carboxylates. More preferred are alkyl, arylalkyl, and halogen containing groups.

n is an integer from 1 to 6, preferably from 1 to 4, more preferably from 1 to 3.

X is nitrogen or phosphorous; Y is selected from the group consisting of nitrogen, oxygen, sulfur, and phosphorus.

Each R can be the same or different and is a bulky substituent. That is, a sterically hindering group with respect to X and Y. Each R can be selected from alkyl (preferably branched), alkenyl (preferably branched), cycloalkyl, heterocyclic (both heteroalkyl and heteroaryl), alkylaryl, arylalkyl, and polymeric, including inorganics such as the P—N ring structures set forth below and inorganic-organic hybrid structures, such as those set forth below. It is preferred that the R substituents contain from 3 to 50, more preferably from 3 to 30, and most preferably from 4 to 20 non-hydrogen atoms. Also, one or more of the carbon or hydrogen positions can be substituted with an element other than carbon and hydrogen, preferably an element selected from Groups 14 to 17, more preferably a Group 14 element such as silicon, a Group 15 element such as nitrogen, a Group 16 element such as oxygen, or a Group 17 halogen.

Non-limiting examples of R include:

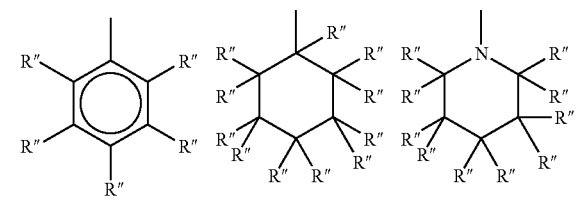

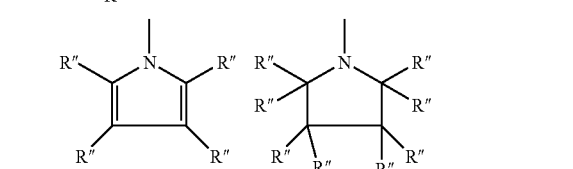

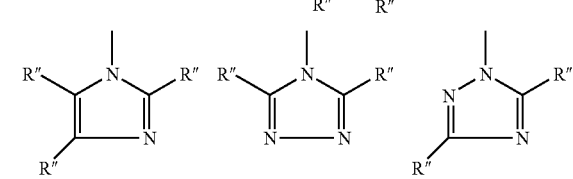

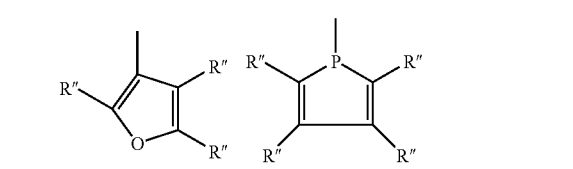

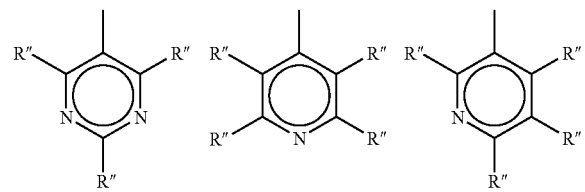

-continued

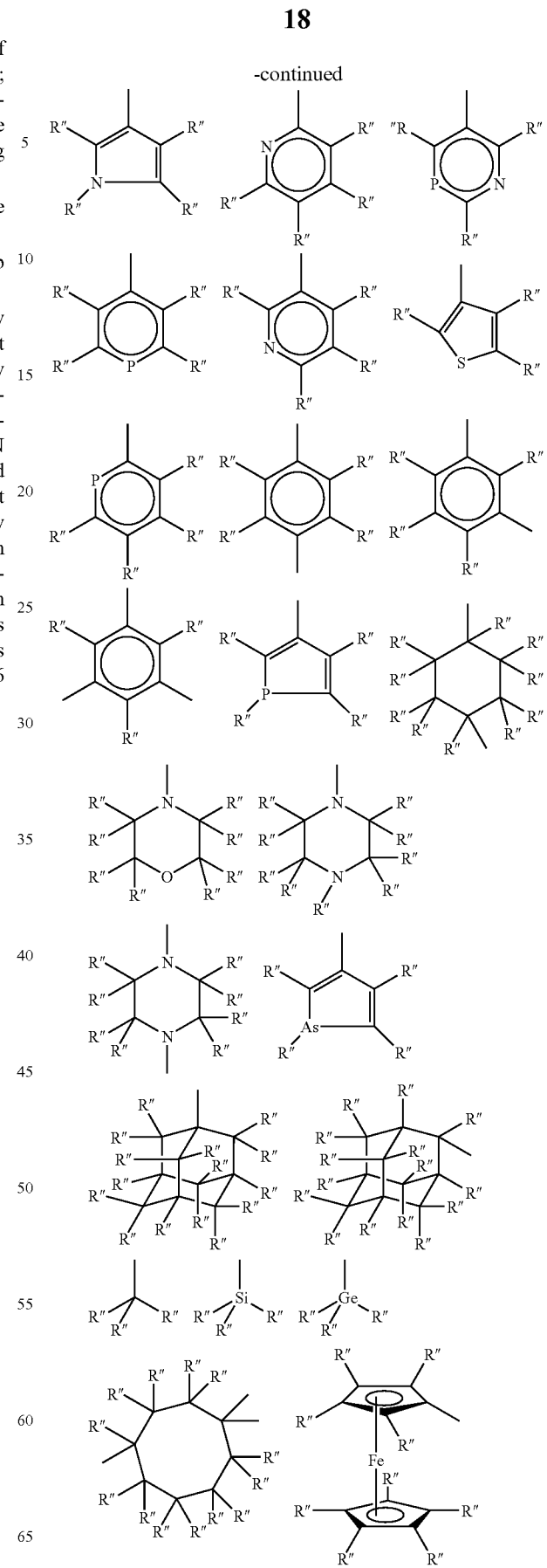

-continued

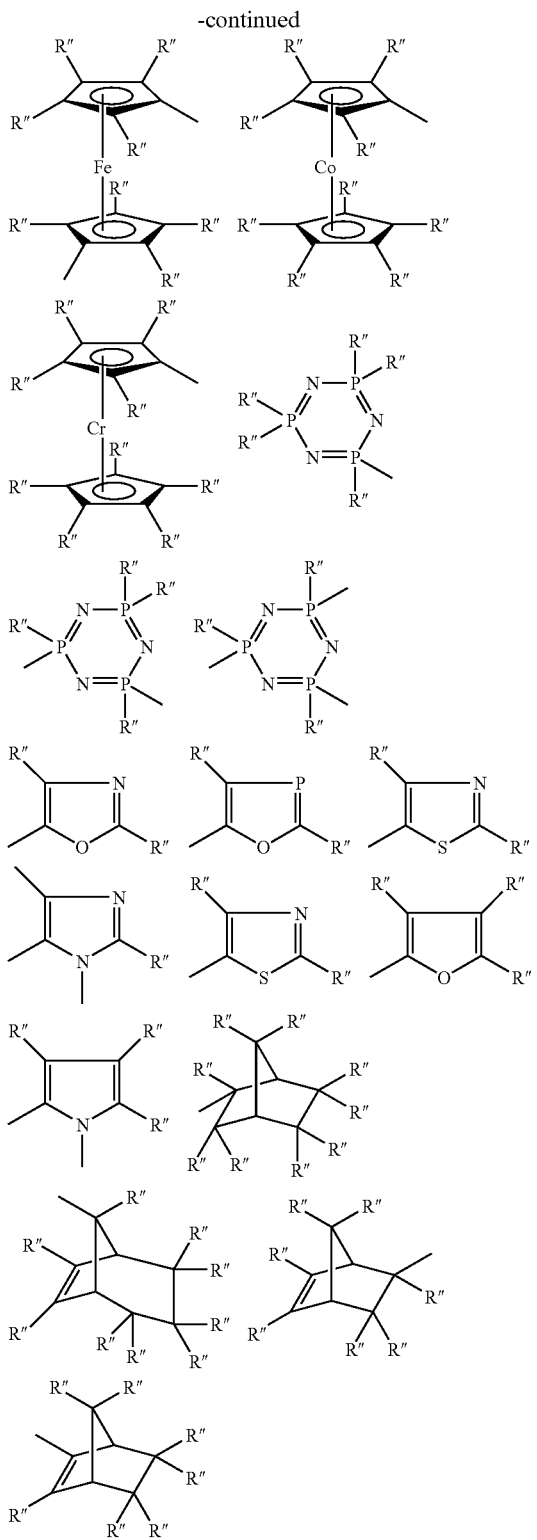

It is preferred that the total number of non-hydrogen atoms for the sum of all R″ groups be up to 40 atoms. It is also preferred that the R″ be selected from hydrogen, halogen, halogen-containing groups, and $C_1$ to $C_{30}$ alkyl, aryl, alkylaryl, arylalkyl, cycloalkyl, and heterocyclic groups as defined above; more preferably R″ is selected from $C_2$ to $C_{20}$ alkyl, aryl, alkylaryl, cycloalkyl, or heterocyclic; and most preferably R″ is a $C_5$ to $C_{20}$ arylalkyl group.

The catalyst precursors can be prepared by any suitable synthesis method and the method of synthesis is not critical to the present invention. One useful method of preparing the catalyst precursors of the present invention is by reacting a suitable metal compound, preferably one having a displaceable anionic ligand, with a heteroatom-containing ligand of this invention. Non-limiting examples of suitable metal compounds include organometallics, metal halides, sulfonates, carboxylates, phosphates, organoborates (including fluoro-containing and other subclasses), acetonacetonates, sulfides, sulfates, tetrafluoroborates, nitrates, perchlorates, phenoxides, alkoxides, silicates, arsenates, borohydrides, naphthenates, cyclooctadienes, diene conjugated complexes, thiocyanates, cyanates, and the metal cyanides. Preferred are the organometallics and the metal halides. More preferred are the organometallics.

As previously mentioned, the metal of the organometal compound is selected from Groups 1 to 16. It is preferred that it be a transition metal selected from the Group 3 to Group 13 elements and Lanthanide series elements. It is more preferred that the metal be selected from the Group 3 to Group 7 elements. The groups referred to are from the Periodic Table of the Elements. It is most preferred that the metal be a Group 4 metal, more particularly preferred is zirconium and hafnium, and most particularly zirconium.

The transition metal compound can, for example, be a metal hydrocarbyl such as: a metal alkyl, a metal aryl, a metal arylalkyl, a metal silylalkyl, a metal diene, a metal amide; or a metal phosphide. Preferably, the transition metal compound is a zirconium or hafnium hydrocarbyl. More preferably, the transition metal compound is a zirconium arylalkyl. Most preferably, the transition metal compound is tetrabenzylzirconium. It is also preferred that the intermediate complexes formed by the present invention correspond to the formula: MX2D(L′)2 wherein M is hafnium or zirconium, X is halide, D is 1,4-diphenyl-1-3-butadiene, and L′ is trimethylphosphine, triethylphosphine, tri-n-propylphosphine, or tri-n-butylphosphine. More preferred intermediate complexes are those wherein X is chloride or bromide.

Non-limiting examples of useful and preferred transition metal compounds include:
(i) tetramethylzirconium, tetraethylzirconium, zirconiumdichloride($\eta^4$-1,4-diphenyl-1,3-butadiene) bis(triethylphosphine), zirconiumdichloride ($\eta^4$-1,4-diphenyl-1,3-butadiene) bis (tri-n-propylphosphine), tetrakis[trimethylsilylmethyl]zirconium, tetrakis[dimethylamino]zirconium, dichlorodibenzylzirconium, chlorotribenzylzirconium, trichlorobenzylzirconium, bis[dimethylamino]bis[benzyl]zirconium, and tetrabenzylzirconium;
(ii) tetramethyltitanium, tetraethyltitanium, titaniumdichloride ($\eta^4$-1,4-diphenyl-1,3-butadiene) bis (triethylphosphine), titaniumdichloride ($\eta^4$-1,4-diphenyl-1,3-butadiene) bis (tri-n-propylphosphine), tetrakis[trimethylsilylmethyl]-titanium, tetrakis[dimethylamino]titanium, dichlorodibenzyltitanium, chlorotribenzyltitanium, trichlorobenzyltitanium, bis[dimethylamino]bis[benzyl]titanium, and tetrabenzyltitanium; and
(iii) tetramethylhafnium, tetraethylhafnium, hafniumdichloride ($\eta^4$-1,4-diphenyl-1,3-butadiene) bis (triethylphosphine), haffiiumdichloride ($\eta^4$-1,4-diphenyl-1,3-butadiene) bis (tri-n-propylphosphine) tetrakis[trimethylsilylmethyl]hafnium, tetrakis[dimethylamino]hafnium, dichlorodibenzylhafnium, chlorotribenzylhafnium, trichlorobenzylhafinium, bis[dimethylamino]bis[benzyl]hafnium, and tetrabenzylhafnium.

One preferred heteroatom-containing ligand that meets the formula:

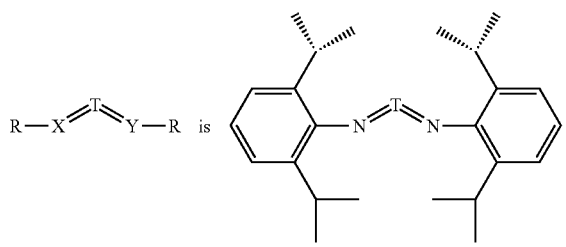

wherein X, Y, T, and R have the meanings stated above, provided Y is selected from the group consisting of nitrogen and phosphorous.

When this ligand is reacted with tetrabenzylzirconium, the corresponding catalyst precursor obtained can be represented by:

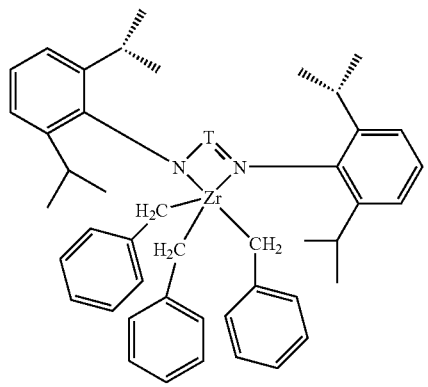

Another preferred heteroatom-containing ligand that meets the formula:

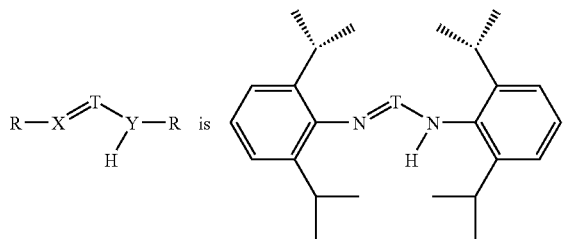

wherein X, Y, T, and R have the meanings stated above, provided Y is selected from the group consisting of nitrogen and phosphorous.

When this ligand is reacted with tetrabenzylzirconium, the corresponding catalyst precursor will be represented by:

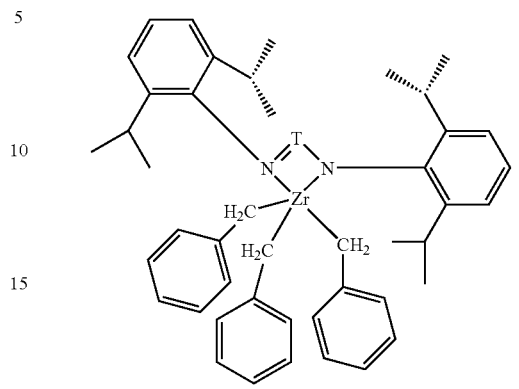

When this ligand is reacted with tetrabenzylzirconium, the catalyst precursor compound formed is represented by the structure below:

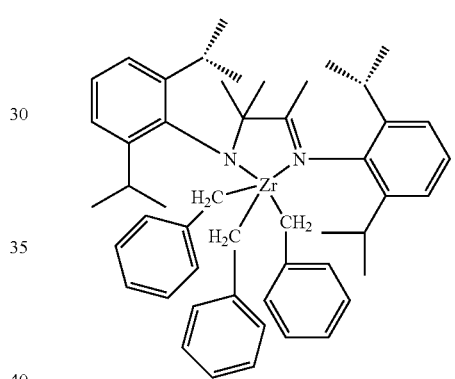

Another preferred heteroatom-containing ligand that meets the formula:

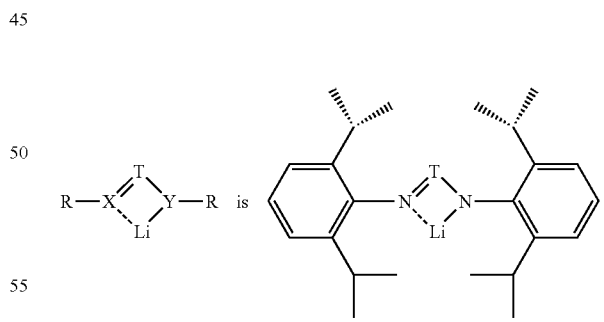

wherein X, Y, T, and R have the meanings stated above, provided Y is selected from the group consisting of nitrogen and phosphorous.

When this ligand is reacted with dichlorodibenzylzirconium (best formed in situ by mixing zirconium tetrachloride and tetrabenzylzirconium is one possibility), several corresponding catalyst precursors are formed and can be represented by:

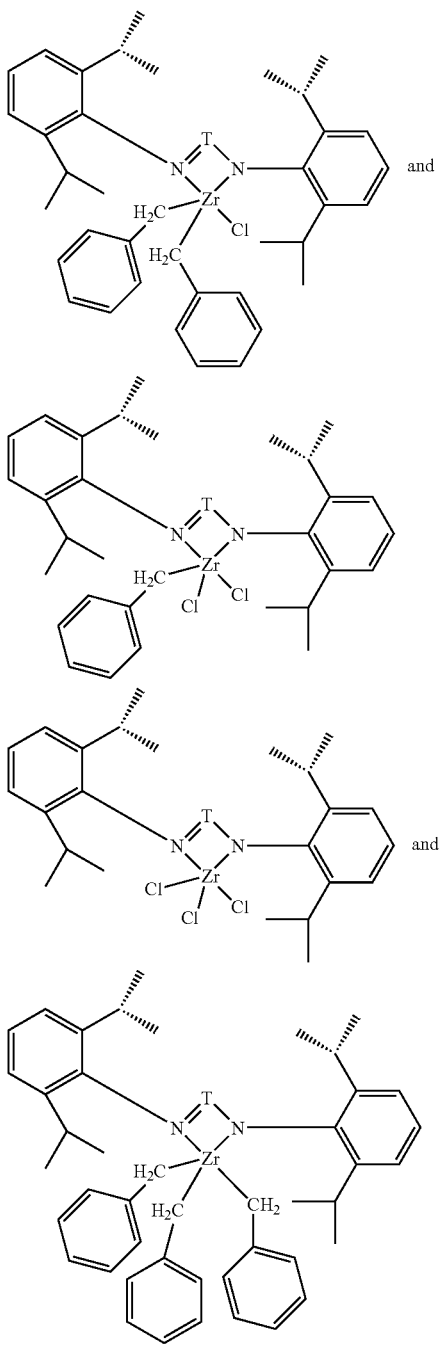

Activators and Activation Methods for Catalyst Compounds

The polymerization catalyst compounds of the invention are typically activated in various ways to yield compounds having a vacant coordination site that will coordinate, insert, and polymerize olefin(s). For the purposes of this patent specification and appended claims, the term "activator" is defined to be any compound which can activate any one of the catalyst compounds described above by converting the neutral catalyst compound to a catalytically active catalyst compound cation. Non-limiting activators, for example, include alumoxanes, aluminum alkyls, ionizing activators, which may be neutral or ionic, and conventional-type cocatalysts.

As used herein, the term "activator" is defined to be any compound or combination of compounds, supported or unsupported, which can activate a catalyst compound precursor, such as by creating a cationic species from the catalyst component. Typically, this involves the abstraction of at least one leaving group (X group in the formulas/structures above) from the metal center of the catalyst component. The catalyst components of the present invention are thus activated towards olefin polymerization using such activators. Embodiments of such activators include Lewis acids such as cyclic or oligomeric poly(hydrocarbylaluminum oxides) and so called non-coordinating activators ("NCA") (alternately, "ionizing activators" or "stoichiometric activators"), or any other compound that can convert a neutral metallocene catalyst component to a metallocene cation that is active with respect to olefin polymerization.

More particularly, it is within the scope of this invention to use Lewis acids such as alumoxane (e.g., "MAO"), modified alumoxane (e.g., "TIBAO"), and alkylaluminum compounds as activators, and/or ionizing activators (neutral or ionic) such as tri (n-butyl)ammonium tetrakis(pentafluorophenyl)boron and/or a trisperfluorophenyl boron metalloid precursors to activate desirable catalyst precursors described herein. MAO and other aluminum-based activators are well known in the art. Ionizing activators are well known in the art and are described by, for example, Eugene You-Xian Chen & Tobin J. Marks, *Cocatalysts for Metal-Catalyzed Olefin Polymerization: Activators, Activation Processes, and Structure-Activity Relationships* 100(4) CHEMICAL REVIEWS 1391–1434 (2000). The activators may be associated with or bound to a support, either in association with the catalyst precursor or separate from the catalyst precursor.

The aluminum alkyl ("alkylaluminum") activator may be described by the formula $AlR^§_3$, wherein $R^§$ is selected from the group consisting of $C_1$ to $C_{20}$ alkyls, $C_1$ to $C_{20}$ alkoxys, halogen (chlorine, fluorine, bromine) $C_6$ to $C_{20}$ aryls, $C_7$ to $C_{25}$ alkylaryls, and $C_7$ to $C_{25}$ arylalkyls. Non-limiting examples of aluminum alkyl compounds which may be utilized as activators for the catalyst precursor compounds for use in the methods of the present invention include trimethylaluminum, triethylaluminum, triisobutylaluminum, tri-n-hexylaluminum, tri-n-octylaluminum and the like.

Non-limiting examples of neutral ionizing activators include Group 13 tri-substituted compounds, in particular, tri-substituted boron, tellurium, aluminum, gallium and indium compounds, and mixtures thereof. The three substituent groups are each independently selected from alkyls, alkenyls, halogen, substituted alkyls, aryls, arylhalides, alkoxy and halides. In one embodiment, the three groups are independently selected from halogen, mono or multicyclic (including halosubstituted) aryls, alkyls, and alkenyl compounds and mixtures thereof. In another embodiment, the three groups are selected from alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls), and combinations thereof. In yet another embodiment, the three groups are selected from alkyls having 1 to 4 carbon groups, phenyl, naphthyl and mixtures thereof. In yet another embodiment, the three groups are selected from highly halogenated alkyls having 1 to 4 carbon groups, highly halogenated phenyls, and highly halogenated naphthyls and mixtures thereof. By "highly halogenated", it is meant that at least 50% of the hydrogens are replaced by a halogen group selected from fluorine, chlorine and bromine. In yet another embodiment, the neutral stoichiometric activator is a tri-substituted Group 13 compound comprising highly fluorided aryl groups, the groups being highly fluorided phenyl and highly fluorided naphthyl groups.

In other non-limiting examples, the neutral tri-substituted Group 13 compounds are boron compounds such as a trisperfluorophenyl boron, trisperfluoronaphthyl boron, tris (3,5-di(trifluoromethyl)phenyl)boron, tris(di-t-butylmethylsilyl)perfluorophenylboron, and other highly fluorinated trisarylboron compounds and combinations thereof, and their aluminum equivalents. Other suitable neutral ionizing activators are described in U.S. Pat. No. 6,399,532 B1, U.S. Pat. No. 6,268,445 B1, and in 19 ORGANOMETALLICS 3332–3337 (2000), and in 17 ORGANOMETALLICS 3996–4003 (1998).

Illustrative, not limiting examples of ionic ionizing activators include trialkyl-substituted ammonium salts such as triethylammonium tetra(phenyl)boron, tripropylammonium tetra(phenyl)boron, tri(n-butyl)ammonium tetra(phenyl)boron, trimethylammonium tetra(p-tolyl)boron, trimethylammonium tetra(o-tolyl)boron, tributylammonium tetra(pentafluorophenyl)boron, tripropylammonium tetra(o,p-dimethylphenyl)boron, tributylammonium tetra(m,m-dimethylphenyl)boron, tributylammonium tetra(p-trifluoromethylphenyl)boron, tributylammonium tetra (pentafluorophenyl)boron, tri(n-butyl)ammonium tetra(o-tolyl)boron and the like; N,N-dialkyl anilinium salts such as N,N-dimethylailinium tetra(phenyl)boron, N,N-diethylanilinium tetra(phenyl)boron, N,N-2,4,6-pentamethylanilinium tetra(phenyl)boron and the like; dialkyl ammonium salts such as di-(isopropyl)ammonium tetra(pentafluorophenyl)boron, dicyclohexylammonium tetra(phenyl)boron and the like; triaryl carbonium salts (trityl salts) such as triphenylcarbonium tetra(phenyl)boron and triphenylcarbonium tetra(pentafluorophenyl)boron; and triaryl phosphonium salts such as triphenylphosphonium tetra(phenyl)boron, triphenylphosphonium tetra(pentafluorophenyl)boron, tri (methylphenyl)phosphonium tetra(phenyl)boron, tri(dimethylphenyl)phosphonium tetra(phenyl)boron and the like, and their aluminum equivalents.

In yet other non-limiting examples of the activators used in the invention, an alkylaluminum can be used in conjunction with a heterocyclic compound. The heterocyclic compound includes at least one nitrogen, oxygen, and/or sulfur atom, and includes at least one nitrogen atom in a particular embodiment. The heterocyclic compound includes 4 or more ring members in one embodiment, and 5 or more ring members in another embodiment.

The heterocyclic compound for use as an activator with an alkylaluminum may be unsubstituted or substituted with one or a combination of substituent groups. Examples of suitable substituents include halogen, alkyl, alkenyl or alkynyl radicals, cycloalkyl radicals, aryl radicals, aryl substituted alkyl radicals, acyl radicals, aroyl radicals, alkoxy radicals, aryloxy radicals, alkylthio radicals, dialkylamino radicals, alkoxycarbonyl radicals, aryloxycarbonyl radicals, carbomoyl radicals, alkyl- or dialkyl-carbamoyl radicals, acyloxy radicals, acylamino radicals, aroylamino radicals, straight, branched or cyclic, alkylene radicals, or any combination thereof. The substituents groups may also be substituted with halogens, particularly fluorine or bromine, heteroatoms or the like. Non-limiting examples of hydrocarbon substituents for the heterocyclic compound include methyl, ethyl, propyl, butyl, pentyl, hexyl, cyclopentyl, cyclohexyl, benzyl or phenyl groups and the like, including all their isomers, for example tertiary butyl, isopropyl, and the like. Other examples of substituents include fluoromethyl, fluoroethyl, difluoroethyl, iodopropyl, bromohexyl or chlorobenzyl.

There may be from 1 to 6 substituents on the heterocyclic compound in one embodiment, and from 1 to 3 in a particular embodiment.

In yet another non-limiting example, one or more positions on the heterocyclic compound are substituted with a halogen atom or a halogen atom containing group, for example a halogenated aryl group. In one embodiment the halogen is selected from chlorine, bromine and fluorine, and selected from fluorine and bromine in another embodiment, and the halogen is fluorine in yet another embodiment. There may be from 1 to 6 halogen substituents in one embodiment, and from 1 to 3 in another embodiment.

Non-limiting examples of heterocyclic compounds that may be utilized with the activator of the invention include substituted and unsubstituted pyrroles, imidazoles, pyrazoles, pyrrolines, pyrrolidines, purines, carbazoles, indoles, phenyl indoles, 2,5-dimethylpyrroles, 3-pentafluorophenylpyrrole, 4,5,6,7-tetrafluoroindole or 3,4-difluoropyrroles.

In one non-limiting example, the heterocyclic compound described above is combined with an alkylaluminum or an alumoxane to yield an activator compound which, upon reaction with a catalyst component, for example a metallocene, produces an active polymerization catalyst. Non-limiting examples of suitable alkylaluminums include trimethylaluminum, triethylaluminum, tiisobutylaluminum, tri-n-hexylaluminum, tri-n-octylaluminum, tri-iso-octylaluminum, triphenylaluminum, and combinations thereof.

Other activators include those described in WO 98/07515 such as tris (2,2',2"-nonafluorobiphenyl)fluoroaluminate. Combinations of activators are also contemplated by the invention, for example, alumoxanes and ionizing activators in combinations. Other activators include aluminum/boron complexes, perchlorates, periodates and iodates including their hydrates; lithium(2,2'-bisphenyl-ditrimethylsilicate) .4THF; silylium salts in combination with a non-coordinating compatible anion. Also, methods of activation such as using radiation, electro-chemical oxidation, and the like are also contemplated as activating methods for the purposes of rendering the neutral metallocene catalyst compound or precursor to a metallocene cation capable of polymerizing olefins. Other activators or methods for activating a metallocene catalyst compound are described in for example, U.S. Pat. Nos. 5,849,852, 5,859,653 and 5,869,723 and WO 98/32775.

A. Alumoxane and Aluminum Alkyl Activators

In one embodiment, alumoxanes activators are utilized as an activator in the catalyst composition of the invention. Alumoxanes are generally oligomeric compounds containing —Al(R)—O— subunits, where R is an alkyl group. Examples of alumoxanes include methylalumoxane (MAO), modified methylalumoxane (MMAO), ethylalumoxane and isobutylalumoxane. Alumoxanes may be produced by the hydrolysis of the respective trialkylaluminum compound. MMAO may be produced by the hydrolysis of trimethylaluminum and a higher trialkylaluminum such as triisobutylaluminum. MMAO's are generally more soluble in aliphatic solvents and more stable during storage. There are a variety of methods for preparing alumoxane and modified alumoxanes, non-limiting examples of which are described in U.S. Pat. Nos. 4,665,208, 4,952,540, 5,091,352, 5,206,199, 5,204,419, 4,874,734, 4,924,018, 4,908,463, 4,968,827, 5,308,815, 5,329,032, 5,248,801, 5,235,081, 5,157,137, 5,103,031, 5,391,793, 5,391,529, 5,693,838, 5,731,253, 5,731,451, 5,744,656, 5,847,177, 5,854,166, 5,856,256 and 5,939,346; and EP-A-0 561 476, EP-B1-0 279 586, EP-A-0

594-218 and EP-B1-0 586 665; and WO 94/10180 and WO 99/15534. A another alumoxane is a modified methyl alumoxane (MMAO) cocatalyst type 3A (commercially available from Akzo Chemicals, Inc. under the trade name Modified Methylalumoxane type 3A).

Aluminum Alkyl or organoaluminum compounds which may be utilized as activators include trimethylaluminum, triethylaluminum, triisobutylaluminum, tri-n-hexylaluminum, tri-n-octylaluminum and the like.

B. Ionizing Activators

It is within the scope of this invention to use an ionizing or stoichiometric activator, neutral or ionic, such as tri(n-butyl)ammonium tetrakis(pentafluorophenyl)borate, a trisperfluorophenyl boron metalloid precursor or a tris(perfluoronaphthyl)boron metalloid precursor, polyhalogenated heteroborane anions (WO 98/43983), boric acid (U.S. Pat. No. 5,942,459) or combination thereof. It is also within the scope of this invention to use neutral or ionic activators alone or in combination with alumoxane or modified alumoxane activators.

Examples of neutral stoichiometric activators include tri-substituted boron, thallium, aluminum, gallium and indium or mixtures thereof. The three substituent groups are each independently selected from alkyls, alkenyls, halogen, substituted alkyls, aryls, arylhalides, alkoxy and halides. Preferably, the three groups are independently selected from halogen, mono or multicyclic (including halosubstituted) aryls, alkyls, and alkenyl compounds and mixtures thereof, preferred are alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls). More preferably, the three groups are alkyls having 1 to 4 carbon groups, phenyl, naphthyl or mixtures thereof. Even more preferably, the three groups are halogenated, preferably fluorinated, aryl groups. Most preferably, the neutral stoichiometric activator is trisperfluorophenyl boron or trisperfluoronaphthyl boron.

Ionic stoichiometric activator compounds may contain an active proton, or some other cation associated with, but not coordinated to, or only loosely coordinated to, the remaining ion of the ionizing compound. Such compounds and the like are described in EP-A-0 570 982, EP-A-0 520 732, EP-A-0 495 375, EP-B1-0 500 944, EP-A-0 277 003 and EP-A-0 277 004; and U.S. Pat. Nos. 5,153,157, 5,198,401, 5,066,741, 5,206,197, 5,241,025, 5,384,299 and 5,502,124.

In a preferred embodiment, the stoichiometric activators include a cation and an anion component, and may be represented by the following formula:

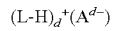

$(L-H)_d^+(A^{d-})$ wherein L is an neutral Lewis base;
H is hydrogen;
$(L-H)^+$ is a Bronsted acid;
$A^{d-}$ is a non-coordinating anion having the charge d−;
d is an integer from 1 to 3.

The cation component, $(L-H)_d^+$ may include Bronsted acids such as protons or protonated Lewis bases or reducible Lewis acids capable of protonating or abstracting a moiety, such as an alkyl or aryl, from the bulky ligand metallocene or Group 15 containing transition metal catalyst precursor, resulting in a cationic transition metal species.

The activating cation $(L-H)_d^+$ may be a Bronsted acid, capable of donating a proton to the transition metal catalytic precursor resulting in a transition metal cation, including ammoniums, oxoniums, phosphoniums, silyliums and mixtures thereof, preferably ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxomiuns from ethers such as dimethyl ether diethyl ether, tetrahydrofuran and dioxane, sulfoniums from thioethers, such as diethyl thioethers and tetrahydrothiophene and mixtures thereof. The activating cation $(L-H)_d^+$ may also be an abstracting moiety such as silver, carboniums, tropylium, carbeniums, ferroceniums and mixtures, preferably carboniums and ferroceniums. Most preferably $(L-H)_d^+$ is triphenyl carbonium.

The anion component $A^{d-}$ include those having the formula $[M^{k+}Q_n]^{d-}$ wherein k is an integer from 1 to 3; n is an integer from 2–6; n−k=d; M is an element selected from Group 13 of the Periodic Table of the Elements, preferably boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than 1 occurrence is Q a halide. Preferably, each Q is a fluorinated hydrocarbyl group having 1 to 20 carbon atoms, more preferably each Q is a fluorinated aryl group, and most preferably each Q is a pentafluoryl aryl group. Examples of suitable $A^{d-}$ also include diboron compounds as disclosed in U.S. Pat. No. 5,447,895.

Most preferably, the ionic stoichiometric activator $(L-H)_d^+ (A^{d-})$ is N,N-dimethylanilinium tetra(perfluorophenyl)borate or triphenylcarbenium tetra(perfluorophenyl)borate.

In one embodiment, an activation method using ionizing ionic compounds not containing an active proton but capable of producing a bulky ligand metallocene catalyst cation and their non-coordinating anion are also contemplated, and are described in EP-A-0 426 637, EP-A-0 573 403 and U.S. Pat. No. 5,387,568.

Supports, Carriers and General Supporting Techniques

Although not preferred, the catalyst system of the invention can include a support material or carrier, or a supported activator. For example, the catalyst compound of the invention can be deposited on, contacted with, vaporized with, bonded to, or incorporated within, adsorbed or absorbed in, or on, a support or carrier.

A. Support Material

A support may also be present as part of the catalyst system of the invention. Supports, methods of supporting, modifying, and activating supports for single-site catalyst such as metallocenes is discussed in, for example, 1 METALLOCENE-BASED POLYOLEFINS 173–218 (J. Scheirs & W. Kaminsky eds., John Wiley & Sons, Ltd. 2000). The terms "support" or "carrier", as used herein, are used interchangeably and refer to any support material, a porous support material in one embodiment, including inorganic or organic support materials. Non-limiting examples of support materials include inorganic oxides and inorganic chlorides, and in particular such materials as talc, clay, silica, alumina, magnesia, zirconia, iron oxides, boria, calcium oxide, zinc oxide, barium oxide, thoria, aluminum phosphate gel, and polymers such as polyvinylchloride and substituted polystyrene, functionalized or crosslinked organic supports such as polystyrene divinyl benzene polyolefins or polymeric compounds, and mixtures thereof, and graphite, in any of its various forms.

The support may be contacted with the other components of the catalyst system in any number of ways. In one embodiment, the support is contacted with the activator to form an association between the activator and support, or a "bound activator". In another embodiment, the catalyst component may be contacted with the support to form a "bound catalyst component". In yet another embodiment, the support may be contacted with the activator and catalyst component together, or with each partially in any order. The components may be contacted by any suitable means as in a solution, slurry, or solid form, or some combination thereof, and may be heated when contacted to from 25° C. to 250° C.

Desirable carriers are inorganic oxides that include Group 2, 3, 4, 5, 13 and 14 oxides and chlorides. Support materials include silica, alumina, silica-alumina, magnesium chloride, graphite, and mixtures thereof in one embodiment. Other useful supports include magnesia, titania, zirconia, montmorillonite (EP 0 511 665 B1), phyllosilicate, and the like. Also, combinations of these support materials may be used, for example, silica-chromium, silica-alumina, silica-titania and the like. Additional support materials may include those porous acrylic polymers described in EP 0 767 184 B1.

In one non-limiting example of the support, graphite is used as the support. The graphite is a powder in one embodiment. In another embodiment, the graphite is flake graphite. In another embodiment, the graphite and has a particle size of from 1 to 500 microns, from 1 to 400 microns in another embodiment, and from 1 to 200 in yet another embodiment, and from 1 to 100 microns in yet another embodiment.

Dehydration or calcining of the support may or may also be carried out. In one embodiment, the support is calcined prior to reaction with the fluorine or other support-modifying compound. In another embodiment, the support is calcined and used without further modification, or calcined, followed by contacting with one or more activators and/or catalyst components. Suitable calcining temperatures range from 100° C. to 1500° C. in one embodiment, and from 200° C. to 1200° C. in another embodiment, and from 300° C. to 1000° C. in another embodiment, and from 350° C. to 900° C. in yet another embodiment, and from 400° C. to 850° C. in yet a more particular embodiment, and from 800° C. to 900° C. in yet a more particular embodiment, and from 810° C. to 890° C. in yet a more particular embodiment, wherein a desirable range comprises any combination of any upper temperature limit with any lower temperature limit. Calcining may take place in the absence of oxygen and moisture by using, for example, an atmosphere of dry nitrogen.

The support, especially an inorganic support or graphite support, may be pretreated such as by a halogenation process or other suitable process that, for example, associates a chemical species with the support either through chemical bonding, ionic interactions, or other physical or chemical interaction. In one embodiment, the support is fluorided. The fluorine compounds suitable for providing fluorine for the support are desirably inorganic fluorine containing compounds. Such inorganic fluorine containing compounds may be any compound containing a fluorine atom as long as it does not contain a carbon atom. Particularly desirable are inorganic fluorine containing compounds selected from the group consisting of $NH_4BF_4$, $(NH_4)_2SiF_6$, $NH_4F$, $(NH_4)_2TaF_7$, $NH_4NbF_4$, $(NH_4)_2GeF_6$, $(NH_4)_2SmF_6$, $(NH_4)_2TiF_6$, $(NH_4)_2ZrF_6$, $MoF_6$, $ReF_6$, $GaF_3$, $SO_2ClF$, $F_2$, $SiF_4$, $SF_6$, $ClF_3$, $ClF_3$, $BrF_5$, $IF_7$, $NF_3$, $HF$, $BF_3$, $NHF_2$ and $NH_4HF_2$.

The support material, if used, can be any of the conventional support materials. Preferably the supported material is a porous support material, for example, talc, inorganic oxides and inorganic chlorides. Other support materials include resinous support materials such as polystyrene, functionalized or crosslinked organic supports, such as polystyrene divinyl benzene polyolefins or polymeric compounds, zeolites, clays, or any other organic or inorganic support material and the like, or mixtures thereof.

The preferred support materials are inorganic oxides that include those Group 2, 3, 4, 5, 13 or 14 metal oxides. The preferred supports include silica, fumed silica, alumina (WO 99/60033), silica-alumina and mixtures thereof. Other useful supports include magnesia, titania, zirconia, magnesium chloride (U.S. Pat. No. 5,965,477), montmorillonite (EP-B1 0 511 665), phyllosilicate, zeolites, talc, clays (U.S. Pat. No. 6,034,187) and the like. Also, combinations of these support materials may be used, for example, silica-chromium, silica-alumina, silica-titania and the like. Additional support materials may include those porous acrylic polymers described in EP 0 767 184 B1. Other support materials include nanocomposites as described in WO 99/47598, aerogels as described in WO 99/48605, spherulites as described in U.S. Pat. No. 5,972,510 and polymeric beads as described in WO 99/50311. A preferred support is fumed silica available under the trade name Cabosil™ TS-610, available from Cabot Corporation. Fumed silica is typically a silica with particles 7 to 30 nanometers in size that has been treated with dimethylsilyldichloride such that a majority of the surface hydroxyl groups are capped.

It is preferred that the support material, most preferably an inorganic oxide, has a surface area in the range of from 10 to 700 $m^2/g$, pore volume in the range of from 0.1 to 4.0 cc/g and average particle size in the range of from 5 to 500 μm. More preferably, the surface area of the support material is in the range of from 50 to 500 $m^2/g$, pore volume of from 0.5 to 3.5 cc/g and average particle size of from 10 to 200 μm. Most preferably the surface area of the support material is in the range is from 100 to 400 $m^2/g$, pore volume from 0.8 to 3.0 cc/g and average particle size is from 5 to 100 μm. The average pore size of the carrier of the invention typically has pore size in the range of from 10 to 1000 Å, preferably 50 to 500 Å, and most preferably 75 to 350 Å.

The support materials may be treated chemically, for example with a fluoride compound as described in WO 00/12565. Other supported activators are described in for example WO 00/13792 that refers to supported boron containing solid acid complex.

In a preferred method of forming a supported catalyst composition component, the amount of liquid in which the activator is present is in an amount that is less than four times the pore volume of the support material, more preferably less than three times, even more preferably less than two times; preferred ranges being from 1.1 times to 3.5 times range and most preferably in the 1.2 to 3 times range. In an alternative embodiment, the amount of liquid in which the activator is present is from one to less than one times the pore volume of the support material utilized in forming the supported activator.

Procedures for measuring the total pore volume of a porous support are well known in the art. Details of one of these procedures is discussed in Volume 1, Experimental Methods in Catalytic Research (Academic Press, 1968) (specifically see pages 67–96). This preferred procedure involves the use of a classical BET apparatus for nitrogen absorption. Another method well known in the art is described in Innes, Total Porosity and Particle Density of Fluid Catalysts By Liquid Titration, 28(3) ANALYTICAL CHEMISTRY 332–334 (March, 1956).

B. Supported Activators

In one embodiment, the catalyst composition includes a supported activator. Many supported activators are described in various patents and publications which include: U.S. Pat. No. 5,728,855 directed to the forming a supported oligomeric alkylaluminoxane formed by treating a trialkylaluminum with carbon dioxide prior to hydrolysis; U.S. Pat. Nos. 5,831,109 and 5,777,143 discusses a supported methylalumoxane made using a non-hydrolytic process; U.S. Pat. No. 5,731,451 relates to a process for making a supported alumoxane by oxygenation with a trialkylsiloxy moiety; U.S. Pat. No. 5,856,255 discusses forming a supported auxiliary catalyst (alumoxane or organoboron compound) at elevated temperatures and pressures; U.S. Pat. No. 5,739,368 discusses a process of heat treating alumoxane and placing it on a support; EP-A-0 545 152 relates to adding a metallocene to a supported alumoxane and adding more methylalumoxane; U.S. Pat. Nos. 5,756,416 and 6,028,151 discuss a catalyst composition of a alumoxane impregnated support and a metallocene and a bulky aluminum alkyl and methylalumoxane; EP-B1-0 662 979 discusses the use of a metallocene with a catalyst support of silica reacted with alumoxane; WO 96/16092 relates to a heated support treated with alumoxane and washing to remove unfixed alumoxane; U.S. Pat. Nos. 4,912,075, 4,937,301, 5,008,228, 5,086,025, 5,147,949, 4,871,705, 5,229,478, 4,935,397, 4,937,217 and 5,057,475, and WO 94/26793 all directed to adding a metallocene to a supported activator; U.S. Pat. No. 5,902,766 relates to a supported activator having a specified distribution of alumoxane on the silica particles; U.S. Pat. No. 5,468,702 relates to aging a supported activator and adding a metallocene; U.S. Pat. No. 5,968,864 discusses treating a solid with alumoxane and introducing a metallocene; EP 0 747 430 A1 relates to a process using a metallocene on a supported methylalumoxane and trimethylaluminum; EP 0 969 019 A1 discusses the use of a metallocene and a supported activator; EP-B2-0 170 059 relates to a polymerization process using a metallocene and a organoaluminum compound, which is formed by reacting aluminum trialkyl with a water containing support; U.S. Pat. No. 5,212,232 discusses the use of a supported alumoxane and a metallocene for producing styrene based polymers; U.S. Pat. No. 5,026,797 discusses a polymerization process using a solid component of a zirconium compound and a water-insoluble porous inorganic oxide preliminarily treated with alumoxane; U.S. Pat. No. 5,910,463 relates to a process for preparing a catalyst support by combining a dehydrated support material, an alumoxane and a polyfunctional organic crosslinker; U.S. Pat. Nos. 5,332,706, 5,473,028, 5,602,067 and 5,420,220 discusses a process for making a supported activator where the volume of alumoxane solution is less than the pore volume of the support material; WO 98/02246 discusses silica treated with a solution containing a source of aluminum and a metallocene; WO 99/03580 relates to the use of a supported alumoxane and a metallocene; EP-A1-0 953 581 discloses a heterogeneous catalytic system of a supported alumoxane and a metallocene; U.S. Pat. No. 5,015,749 discusses a process for preparing a polyhydrocarbyl-alumoxane using a porous organic or inorganic imbiber material; U.S. Pat. Nos. 5,446,001 and 5,534,474 relates to a process for preparing one or more alkylaluminoxanes immobilized on a solid, particulate inert support; and EP-A1-0 819 706 relates to a process for preparing a solid silica treated with alumoxane. Also, the following articles include: W. Kaminsky, et al., Polymerization of Styrene with Supported Half-Sandwich Complexes, 37 JOURNAL OF POLYMER SCIENCE 2959–2968 (1999) describes a process of adsorbing a methylalumoxane to a support followed by the adsorption of a metallocene; Junting Xu, et al. Characterization of isotactic polypropylene prepared with dimethylsilyl bis(1-indenyl)zirconium dichloride supported on methylaluminoxane pretreated silica, 35 EUROPEAN POLYMER JOURNAL 1289–1294 (1999), discusses the use of silica treated with methylalumoxane and a metallocene; Stephen O'Brien, et al., EXAFS analysis of a chiral alkene polymerization catalyst incorporated in the mesoporous silicate MCM-41, CHEM. COMMUN. 1905–1906 (1997) discloses an immobilized alumoxane on a modified mesoporous silica; and F. Bonini, et al., Propylene Polymerization through Supported Metallocene/MAO Catalysts: Kinetic Analysis and Modeling, 33 JOURNAL OF POLYMER SCIENCE 2393–2402 (1995) discusses using a methylalumoxane supported silica with a metallocene. Any of the methods discussed in these references are useful for producing the supported activator component utilized in the catalyst composition of the invention.

In another embodiment, the supported activator, such as supported alumoxane, is aged for a period of time prior to use herein. For reference please refer to U.S. Pat. Nos. 5,468,702 and 5,602,217.

In an embodiment, the supported activator is in a dried state or a solid. In another embodiment, the supported activator is in a substantially dry state or a slurry, preferably in a mineral oil slurry.

In another embodiment, two or more separately supported activators are used, or alternatively, two or more different activators on a single support are used.

In another embodiment, the support material, preferably partially or totally dehydrated support material, preferably 200° C. to 600° C. dehydrated silica, is then contacted with an organoaluminum or alumoxane compound. Preferably in an embodiment where an organoaluminum compound is used, the activator is formed in situ on and in the support material as a result of the reaction of, for example, trimethylaluminum and water.

In another embodiment, Lewis base-containing supports are reacted with a Lewis acidic activator to form a support bonded Lewis acid compound. The Lewis base hydroxyl groups of silica are exemplary of metal/metalloid oxides where this method of bonding to a support occurs.

Other embodiments of supporting an activator are described in U.S. Pat. No. 5,427,991, where supported non-coordinating anions derived from trisperfluorophenyl boron are described; U.S. Pat. No. 5,643,847 discusses the reaction of Group 13 Lewis acid compounds with metal oxides such as silica and illustrates the reaction of trisperfluorophenyl boron with silanol groups (the hydroxyl groups of silicon) resulting in bound anions capable of protonating transition metal organometallic catalyst compounds to form catalytically active cations counter-balanced by the bound anions; immobilized Group IIIA Lewis acid catalysts suitable for carbocationic polymerizations are described in U.S. Pat. No. 5,288,677; and James C. W. Chien, 29 J. POLY. SCI.: PT A: POLY. CHEM. 1603–1607 (1991), describes the olefin polymerization utility of methylalumoxane (MAO) reacted with silica ($SiO^2$) and metallocenes and describes a covalent bonding of the aluminum atom to the silica through an oxygen atom in the surface hydroxyl groups of the silica.

In a preferred embodiment, a supported activator is formed by preparing in an agitated, and temperature and pressure controlled vessel a solution of the activator and a suitable solvent, then adding the support material at temperatures from 0° C. to 100° C., contacting the support with the activator solution for up to 24 hours, then using a combination of heat and pressure to remove the solvent to produce a free flowing powder. Temperatures can range from 40° C. to 120° C. and pressures from 5 psia to 20 psia (34.5 to 138 kPa). An inert gas sweep can also be used in assist in removing solvent. Alternate orders of addition, such as slurrying the support material in an appropriate solvent then adding the activator, can be used.

Polymerization Process

The catalyst systems prepared and the method of catalyst system addition described above are suitable for use in any prepolymerization and/or polymerization process over a wide range of temperatures and pressures. The temperatures may be in the range of from −60° C. to 280° C., preferably from 50° C. to 200° C., and the pressures employed may be in the range from 1 atmosphere to 500 atmospheres or higher.

Polymerization processes include solution, gas phase, slurry phase and a high pressure process or a combination thereof. Particularly preferred is a gas phase or slurry phase polymerization of one or more olefins at least one of which is ethylene or propylene.

In one embodiment, the process of this invention is directed toward a solution, high pressure, slurry or gas phase polymerization process of one or more olefin monomers having from 2 to 30 carbon atoms, preferably 2 to 12 carbon atoms, and more preferably 2 to 8 carbon atoms. The invention is particularly well suited to the polymerization of two or more olefin monomers of ethylene, propylene, 1-butene, 1-pentene, 4-methyl-1-pentene, 1-hexene, 1-octene and 1-decene.

Other monomers useful in the process of the invention include ethylenically unsaturated monomers, diolefins having 4 to 18 carbon atoms, conjugated or nonconjugated dienes, polyenes, vinyl monomers and cyclic olefins. Non-limiting monomers useful in the invention may include norbornene, norbornadiene, isobutylene, isoprene, vinylbenzocyclobutane, styrenes, alkyl substituted styrene, ethylidene norbornene, dicyclopentadiene and cyclopentene.

In the most preferred embodiment of the process of the invention, a copolymer of ethylene is produced, where with ethylene, a comonomer having at least one alpha-olefin having from 3 to 15 carbon atoms, preferably from 4 to 12 carbon atoms, and most preferably from 4 to 8 carbon atoms, is polymerized in a gas phase process.

In another embodiment of the process of the invention, ethylene or propylene is polymerized with at least two different comonomers, optionally one of which may be a diene, to form a terpolymer.

In an embodiment, the mole ratio of comonomer to ethylene, $C_x/C_2$, where $C_x$ is the amount of comonomer and $C_2$ is the amount of ethylene is between 0.001 to 0.200 and more preferably between 0.002 to 0.008.

In one embodiment, the invention is directed to a polymerization process, particularly a gas phase or slurry phase process, for polymerizing propylene alone or with one or more other monomers including ethylene, and/or other olefins having from 4 to 12 carbon atoms. Polypropylene polymers may be produced using the particularly bridged bulky ligand metallocene catalysts as described in U.S. Pat. Nos. 5,296,434 and 5,278,264.

Typically in a gas phase polymerization process a continuous cycle is employed where in one part of the cycle of a reactor system, a cycling gas stream, otherwise known as a recycle stream or fluidizing medium, is heated in the reactor by the heat of polymerization. This heat is removed from the recycle composition in another part of the cycle by a cooling system external to the reactor. Generally, in a gas fluidized bed process for producing polymers, a gaseous stream containing one or more monomers is continuously cycled through a fluidized bed in the presence of a catalyst under reactive conditions. The gaseous stream is withdrawn from the fluidized bed and recycled back into the reactor. Simultaneously, polymer product is withdrawn from the reactor and fresh monomer is added to replace the polymerized monomer. (See for example U.S. Pat. Nos. 4,543,399, 4,588,790, 5,028,670, 5,317,036, 5,352,749, 5,405,922, 5,436,304, 5,453,471, 5,462,999, 5,616,661 and 5,668,228)

The reactor pressure in a gas phase process may vary from 100 psig (690 kPa) to 600 psig (4138 kPa), preferably in the range of from 200 psig (1379 kPa) to 400 psig (2759 kPa), more preferably in the range of from 250 psig (1724 kPa) to 350 psig (2414 kPa).

The reactor temperature in a gas phase process may vary from 30° C. to 120° C., preferably from 60° C. to 115° C., more preferably in the range of from 70° C. to 110° C., and most preferably in the range of from 70° C. to 95° C.

Other gas phase processes contemplated by the process of the invention include series or multistage polymerization processes. Also gas phase processes contemplated by the invention include those described in U.S. Pat. Nos. 5,627, 242, 5,665,818 and 5,677,375; and EP-A-0 794 200 EP-B1-0 649 992, EP-A-0 802 202 and EP-B-634 421.

In a preferred embodiment, the reactor utilized in the present invention is capable of and the process of the invention is producing greater than 500 lbs of polymer per hour (227 Kg/hr) to 200,000 lbs/hr (90,900 Kg/hr) or higher of polymer, preferably greater than 1000 lbs/hr (455 Kg/hr), more preferably greater than 10,000 lbs/hr (4540 Kg/hr), even more preferably greater than 25,000 lbs/hr (11,300 Kg/hr), still more preferably greater than 35,000 lbs/hr (15,900 Kg/hr), still even more preferably greater than 50,000 lbs/hr (22,700 Kg/hr) and most preferably greater than 65,000 lbs/hr (29,000 Kg/hr) to greater than 100,000 lbs/hr (45,500 Kg/hr).

A slurry polymerization process generally uses pressures in the range of from 1 to 50 atmospheres and even greater and temperatures in the range of 0° C. to 120° C. In a slurry polymerization, a suspension of solid, particulate polymer is formed in a liquid polymerization diluent medium to which ethylene and comonomers and often hydrogen along with catalyst are added. The suspension including diluent is intermittently or continuously removed from the reactor where the volatile components are separated from the polymer and recycled, optionally after a distillation, to the reactor. The liquid diluent employed in the polymerization medium is typically an alkane having from 3 to 7 carbon atoms, preferably a branched alkane. The medium employed should be liquid under the conditions of polymerization and relatively inert. When a propane medium is used the process must be operated above the reaction diluent critical temperature and pressure. Preferably, a hexane or an isobutane medium is employed.

A preferred polymerization technique of the invention is referred to as a particle form polymerization, or a slurry process where the temperature is kept below the temperature at which the polymer goes into solution. Such technique is well known in the art, and described in for instance U.S. Pat. No. 3,248,179. Other slurry processes include those employing a loop reactor and those utilizing a plurality of stirred reactors in series, parallel, or combinations thereof. Non-limiting examples of slurry processes include continuous loop or stirred tank processes. Also, other examples of slurry processes are described in U.S. Pat. Nos. 4,613,484 and 5,986,021.

In an embodiment the reactor used in the slurry process of the invention is capable of and the process of the invention is producing greater than 2000 lbs of polymer per hour (907 Kg/hr), more preferably greater than 5000 lbs/hr (2268 Kg/hr), and most preferably greater than 10,000 lbs/hr (4540 Kg/hr). In another embodiment the slurry reactor used in the process of the invention is producing greater than 15,000 lbs of polymer per hour (6804 Kg/hr), preferably greater than 25,000 lbs/hr (11,340 Kg/hr) to 100,000 lbs/hr (45,500 Kg/hr). Examples of solution processes are described in U.S. Pat. Nos. 4,271,060, 5,001,205, 5,236,998, 5,589,555 and 5,977,251; and WO 99/32525 and WO 99/40130.

A preferred process of the invention is where the process, preferably a slurry or gas phase process is operated in the presence of a bulky ligand metallocene catalyst system of the invention and in the absence of or essentially free of any scavengers, such as triethylaluminum, trimethylaluminum, tri-isobutylaluminum and tri-n-hexylaluminum and diethyl aluminum chloride, dibutyl zinc and the like. This preferred process is described in WO 96/08520 and U.S. Pat. Nos. 5,712,352 and 5,763,543.

In one embodiment of the invention, olefin(s), preferably $C_2$ to $C_{30}$ olefin(s) or alpha-olefin(s), preferably ethylene or propylene or combinations thereof are prepolymerized in the presence of the metallocene catalyst systems of the invention described above prior to the main polymerization. The prepolymerization can be carried out batchwise or continuously in gas, solution or slurry phase including at elevated pressures. The prepolymerization can take place with any olefin monomer or combination and/or in the presence of any molecular weight controlling agent such as hydrogen. For examples of prepolymerization procedures, see U.S. Pat. Nos. 4,748,221, 4,789,359, 4,923,833, 4,921,825, 5,283,278 and 5,705,578; and EP-B-0279 863; and WO 97/44371.

In one embodiment, toluene is not used in the preparation or polymerization process of this invention.

Polymer Products

The polymers produced by the process of the invention can be used in a wide variety of products and end-use applications. The polymers produced by the process of the invention include linear low-density polyethylene, elastomers, plastomers, high density polyethylenes, medium density polyethylenes, low density polyethylenes, polypropylene and polypropylene copolymers. Also produced are isotactic polymers, such as poly-1-hexene.

The polymers, typically ethylene based polymers, have a density in the range of from 0.86 g/cc to 0.97 g/cc, preferably in the range of from 0.88 g/cc to 0.965 g/cc, more preferably in the range of from 0.900 g/cc to 0.96 g/cc, even more preferably in the range of from 0.905 g/cc to 0.95 g/cc, yet even more preferably in the range from 0.910 g/cc to 0.940 g/cc, and most preferably greater than 0.915 g/cc, preferably greater than 0.920 g/cc, and most preferably greater than 0.925 g/cc. Density is measured in accordance with ASTM-D-1238.

The polymers produced by the process of the invention typically have a molecular weight distribution, a weight average molecular weight to number average molecular weight ($M_w/M_n$) of greater than 1.5 to 30, particularly greater than 2 to 10, more preferably greater than 2.2 to less than 8, and most preferably from 2.5 to 8.

Also, the polymers of the invention typically have a narrow composition distribution as measured by Composition Distribution Breadth Index (CDBI). Further details of determining the CDBI of a copolymer are known to those skilled in the art. See, for example WO 93/03093.

The polymers of the invention in one embodiment have CDBI's generally in the range of greater than 50% to 100%, preferably 99%, preferably in the range of 55% to 85%, and more preferably 60% to 80%, even more preferably greater than 60%, still even more preferably greater than 65%.

In another embodiment, polymers produced using a catalyst system of the invention have a CDBI less than 50%, more preferably less than 40%, and most preferably less than 30%.

The polymers of the present invention in one embodiment have a melt index (MI) or ($I_2$) as measured by ASTM-D-1238-E in the range from no measurable flow to 1000 dg/min, more preferably from 0.01 dg/min to 100 dg/min, even more preferably from 0.1 dg/min to 50 dg/min, and most preferably from 0.1 dg/min to 10 dg/min.

The polymers of the invention in an embodiment have a melt index ratio ($I_{21}/I_2$) ($I_{21}$ is measured by ASTM-D-1238-F) of from 10 to less than 25, more preferably from 15 to less than 25.

The polymers of the invention in a preferred embodiment have a melt index ratio ($I_{21}/I_2$) of from preferably greater than 25, more preferably greater than 30, even more preferably greater that 40, still even more preferably greater than 50 and most preferably greater than 65. In an embodiment, the polymer of the invention may have a narrow molecular weight distribution and a broad composition distribution or vice-versa, and may be those polymers described in U.S. Pat. No. 5,798,427.

In yet another embodiment, propylene based polymers are produced in the process of the invention. These polymers include atactic polypropylene, isotactic polypropylene, hemi-isotactic and syndiotactic polypropylene. Other propylene polymers include propylene block or impact copolymers. Propylene polymers of these types are well known in the art see for example U.S. Pat. Nos. 4,794,096, 3,248,455, 4,376,851, 5,036,034 and 5,459,117.

The polymers of the invention may be blended and/or co-extruded with any other polymer. Non-limiting examples of other polymers include linear low density polyethylenes, elastomers, plastomers, high pressure low density polyethylene, high density polyethylenes, polypropylenes and the like.

Polymers produced by the process of the invention and blends thereof are useful in such forming operations as film, sheet, and fiber extrusion and co-extrusion as well as blow molding, injection molding and rotary molding. Films include blown or cast films formed by co-extrusion or by lamination useful as shrink film, cling film, stretch film, sealing films, oriented films, snack packaging, heavy duty bags, grocery sacks, baked and frozen food packaging, medical packaging, industrial liners, membranes, etc. in food-contact and non-food contact applications. Fibers include melt spinning, solution spinning and melt blown fiber operations for use in woven or non-woven form to make filters, diaper fabrics, medical garments, geotextiles, etc. Extruded articles include medical tubing, wire and cable coatings, pipe, geomembranes, and pond liners. Molded articles include single and multi-layered constructions in the form of bottles, tanks, large hollow articles, rigid food containers and toys, etc.

The present invention will be illustrated in more detail with reference to the following examples, which should not be construed to be limiting in scope of the present invention.

Glossary

Activity is measured in g of polyethylene/mmol of metal per hr at 100 psig ethylene.

$I_2$ is the flow index (dg/min) as measured by ASTM D-1238-Condition E at 190° C.

$I_{21}$ is the flow index (dg/min) as measured by ASTM D-1238-Condition F.

MFR is the Melt Flow Ratio, $I_{21}/I_2$.

MMAO is a solution of modified methylalumoxane in heptane, approximately 1.9 molar in aluminum, commercially available from Akzo Chemicals, Inc. (type 3).

BBF is Butyl Branching Frequency, number of butyl branches per 1000 main chain carbon atoms, as determined by infrared measurement techniques.

$M_w$ is Weight Average Molecular Weight, as determined by gel permeation chromatography using crosslinked polystyrene columns; pore size sequence: 1 column less than 1000 Å, 3 columns of mixed 5×107 Å; 1,2,4-trichlorobenzene solvent at 140° C., with refractive index detection. $M_n$ is number average molecular weight.

PDI is the Polydispersity Index, equivalent to Molecular Weight Distribution ($M_w/M_n$).

EXAMPLES

Preparation of Tetrakis(trimethylsilylmethyl)zirconium

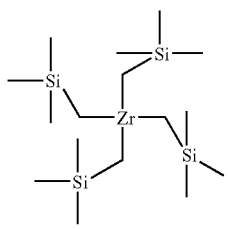

Tetrakis(trimethylsilylmethyl)zirconium was prepared following Collier, M. R., Lappert, M. F., Pearce, R., *Silylmethyl and Related Complexes. Part I. Kinetically stable Alkyls of Ti(IV), Zr(IV) and Hf(IV)* J. C. S. DALTON 745 (1973).

Preparation of diacetyl-bis(2,6-diisopropylphenylimine) diazabutadiene

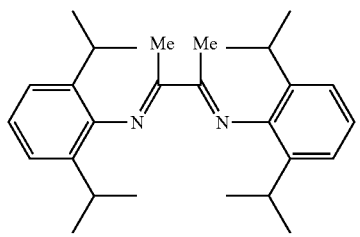

General procedure: Into a 300 mL flask equipped with a stir bar was charged 100 mmol 2,6-diisopropylaniline and 100 mL methanol. The solution was chilled to 0° C. and 0.19 mL formic acid was added to the stirring solution. When the solution reached room temperature (RT) 50 mmol 2,3-butanedione was added. The solution was allowed to stir overnight, then filtered to collect the yellow solids. The crude product was dissolved in hexane and dried over $Na_2SO_4$. The mixture was filtered and the filtrate vacuum stripped. The solids were then recrystallized from methanol/ethanol.

Monoalkylation of the Diazabutadiene

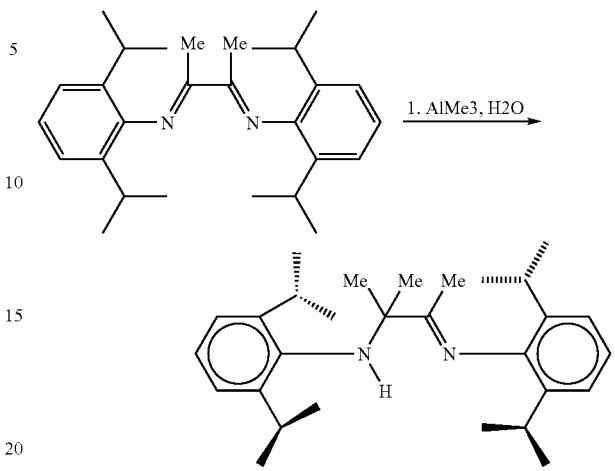

General procedure: Diacetyl-bis(2,6-diisopropylphenylimine) (25 mmol, 10 g) was dissolved in 25 mL toluene in a 100 mL Schlenk flask equipped with a stir bar and septa and chilled to 0° C. Trimethyl aluminum (25 mmol (12.5 mL) Aldrich, [2.0M soln in toluene]) was charged drop-wise via syringe. The reaction was allowed to slowly warm to room temperature with stirring. When complete, the reaction was hydrolyzed with $NaOH/H_2O$ and extracted with ether. The ether extracts were dried over $MgSO_4$ and filtered. The filtrate was vacuum stripped to a viscous orange residue.

Attempted reaction of monoalkylated diazabutadiene with $(Me_3SiCH_2)_4Zr$

General procedure: In a dry box, tetrakis(trimethylsilylmethyl)zirconium was charged to a 7 mL amber bottle equipped with a stir bar and screw cap. The monoalkylated diazabutadiene was charged to a vial. Benzene-$d_6$ (0.75 mL) was added to both vessels. The monoalkylated diazabutadiene solution was slowly transferred via pipette into the stirring zirconium solution. The reaction bottle was capped and allowed to stir for 18 hours at room temperature in the dry box. The solution was submitted for testing in the 1 L slurry reactor. An aliquot to this reaction solution exhibited good ethylene polymerization activities at 85° C. with MMAO cocatalyst. The carbon dimethyl bridged iminoamideZr[$CH_2SiMe_3]_3$ compound is most likely present with other products as well. This result is attributed to a more optimized bridge. Hydrogen was an effective chain-transfer agent that does not appear to adversely affect catalyst activity.

Attempted Reaction of Monoalkylated Diazabutadiene with Tetrabenzyl Zirconium

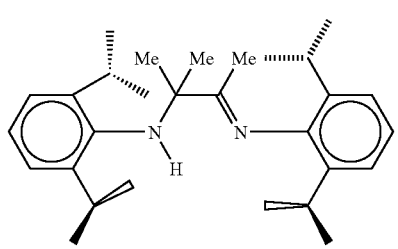

General procedure: In a dry box, tetrabenzyl zirconium (0.200 mmol, 0.091 g,) was charged to a 7 mL amber bottle equipped with a stir bar and screw cap. The monoalkylated compound was charged to a vial. Benzene-$d_6$ (1.5 mL) was added to both vessels. The monoalkylated diazabutadiene solution was slowly transferred via pipette into the stirring zirconium solution. The reaction bottle was capped and allowed to stir for 18 hours at room temperature in the dry box. $^1$H-NMR analysis of reaction solution confirmed very little if any reaction occurred.

Hydrolysis of the Monoalkylated Diazabutadiene to Keto-Amine

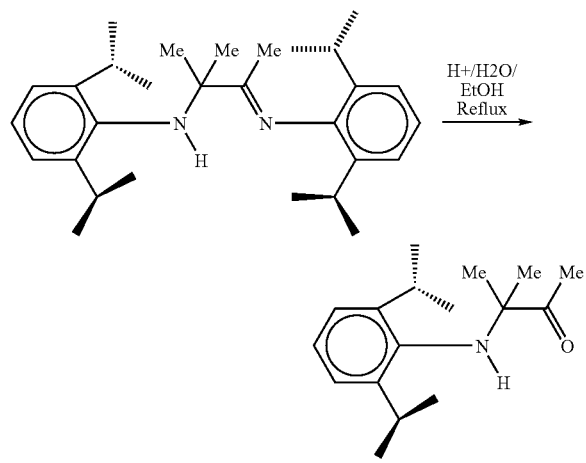

General procedure: Monoalkylated diazabutadiene (150.0 mmol, 60 g) was charged to a 3 L 3-neck round-bottom flask equipped with a stir bar. A 750 mL addition funnel was attached to the reaction flask. Ethanol (750 mL) was added through the addition funnel to dissolve the monoalkylated compound. When completed dissolved, 250 mL water was added. Sulfuric acid (600 mmol, 600 mL of 1.0M soln in $H_2O$) was charged over a 1 hr. period to the addition funnel. A reflux condenser was then attached to the reaction flask and the reaction was heated to 85° C. and allowed to reflux for 1 hour.

When the reaction was complete, the reaction solution was transferred into a 4L beaker equipped with a stir bar. Sodium hydroxide pellets were slowly added to the stirring solution until the pH reached 9.0. The solution was then extracted with toluene. The extracts were dried over $MgSO_4$, filtered and the filtrate vacuum stripped to a viscous yellow residue, than vacuum distilled with a short-path distillation apparatus.

The product was confirmed by$^1$H-NMR in Benzene-$d_6$.

Reaction of Monoalkylated Diazabutadiene with butyl lithium

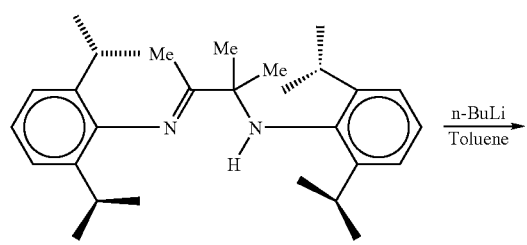

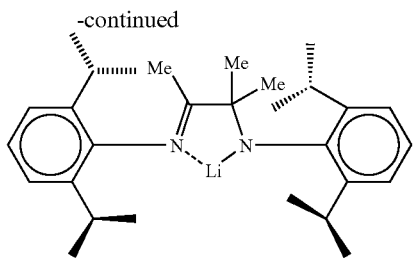

General procedure: In a the dry box monoalkylated diazabutadiene (25 mmol, 10.5 g) was charged to a 100 mL Schlenk flask equipped with a stir bar and septum. Toluene (25 mL) was added to dissolve compound. Butyl lithium (10 mL, Aldrich, [2.5M solution in hexanes]) was slowly added. When the reaction was completed, the white solids were filtered from the orange solvent layer.

Reaction of the Lithium Salt of Monoalkylated Diazabutadiene with $CrCl_3$

General procedure: Chromium (III) chloride (0.400 mmol, 0.063 g, Aldrich) was charged to a 7 mL amber bottle equipped with a stir bar and cap. Toluene (3 mL) was added. The lithium salt of monoalkylated diazabutadiene (0.400 mmol, 0.171 g) was dissolved in 3.0 mL toluene and transferred into the stirring $CrCl_3$/toluene. The reaction was allowed to stir at room temperature in the dry box for 8 weeks. The solvent layer was decanted from the moderate amount of white solids and submitted for polymerization testing.

Reaction of Monoalkylated Diazabutadiene with Tetrabenzyl Zirconium/Zirconium (IV) Chloride

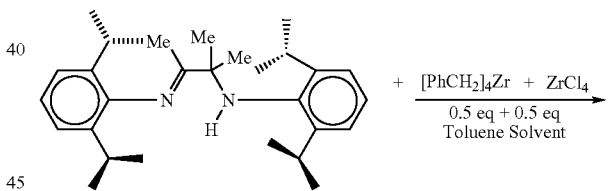

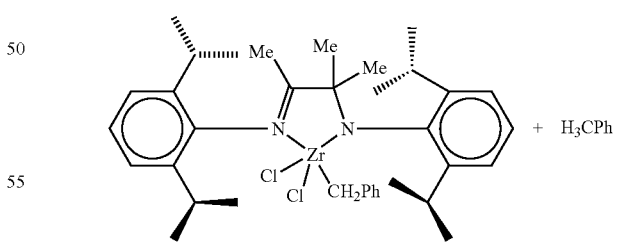

General procedure: Tetrabenzyl zirconium (25 mmol, 11.4 g) and 200 mL toluene were charged to a 500 mL bottle. The tetrabenzyl zirconium solution was transferred into the stirring zirconium (IV) chloride slurry and allowed to stir at room temperature for one hour. A solution of monoalkylated diazabutadiene (50 mmol, 21.0 g) in 2000 mL of toluene was transferred into the stirring tetrabenzyl zirconium solution. A zirconium (IV) chloride (25 mmol, 5.3 g) and 200 mL toluene slurry was transferred into the stirring solution. The mixture was allowed to stir at room temperature for 4 days. Toluene (600 mL) was added to the reaction solution.

Reaction of Lithium Salt of Monoalkylated Diazabutadiene with Tetrabenzyl Zirconium/Zirconium (IV) Chloride

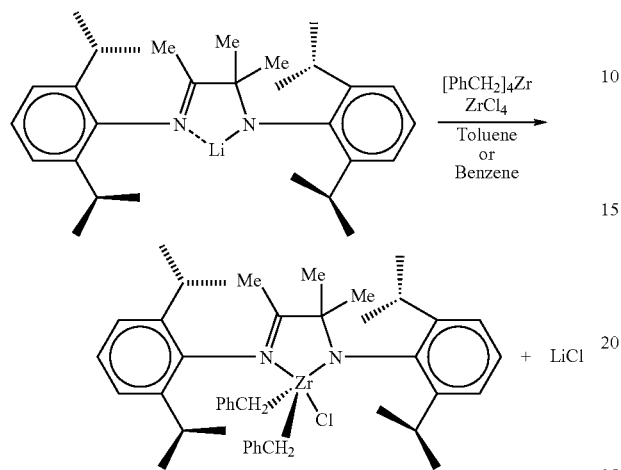

General procedure: Zirconium (IV) chloride (0.050 mmol, 0.012 g) was charged to a 7 mL amber bottle equipped with a stir bar and cap. Tetrabenzyl zirconium (0.150 mmol, 0.068 g, [455.75]) was charged to a second bottle the lithium salt of monoalkylated diazabutadiene (0.200 mmol, 0.085 g) was charged to a third bottle. Benzene-$d_6$ (1.0 ml) was added to each bottle. The lithium salt of monoalkylated diazabutadiene solution was transferred into the tetrabenzyl zirconium solution. The combined solution was transferred into the stirring slurry of $ZrCl_4$. The mixture was allowed to stir at room temperature overnight.

Reaction of the Lithium Salt of Monoalkylated Diazabutadiene with Tetrabenzyl Hafnium/Hafnium(IV) Chloride

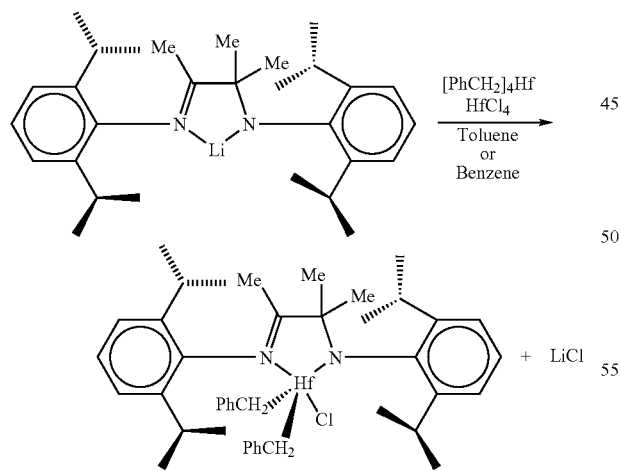

General procedure: Hafnium (IV) chloride (0.100 mmol, 0.032 g) was charged to a 7 mL amber bottle equipped with a stir bar and cap. Tetrabenzyl hafnium (0.100 mmol, 0.054 g) was charged to a second bottle. The lithium salt of monoalkylated diazabutadiene (0.200 mmol, 0.085 g) was charged to a third bottle. Benzene-$d_6$ (1.0 ml) was added to each bottle. The lithium salt of monoalkylated diazabutadiene solution was transferred into the tetrabenzyl hafnium solution. The combined solution was transferred into the stirring slurry of $HfCl_4$. The mixture was allowed to stir at room temperature overnight.

Reaction of Lithium Salt of Monoalkylated Diazabutadiene with Tetrabenzyl Zirconium/Zirconium (IV) Chloride

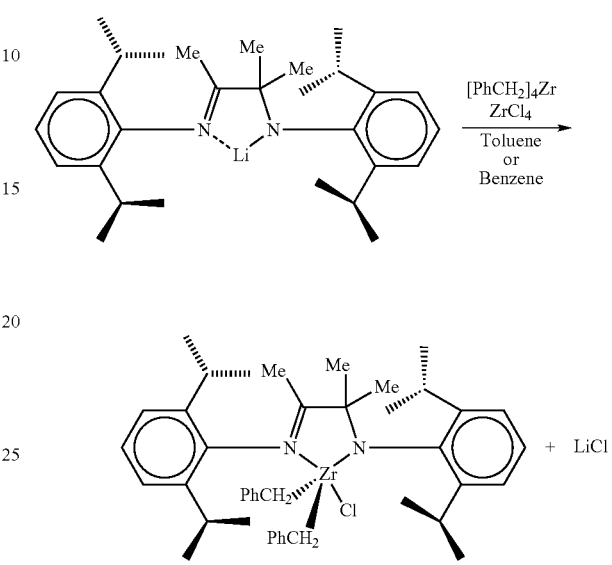

General procedure: Zirconium (IV) chloride (0.100 mmol, 0.023 g) was charged to a 7 mL amber bottle equipped with a stir bar and cap. Tetrabenzyl zirconium (0.100 mmol, 0.046 g, was charged to a second bottle. The lithium salt of monoalkylated diazabutadiene (0.200 mmol, 0.085 g) was charged to a third bottle. Benzene-$d_6$ (1.0 ml) was added to each bottle. The 8-REMU-022 solution was transferred into the Tetrabenzyl zirconium solution. The combined solution was transferred into the stirring slurry of $ZrCl_4$. The mixture was allowed to stir at room temperature overnight.

The 50:50 mole ratio of tetrabenzylzirconium and zirconium tetrachloride was evaluated to produce the dibenzylchloro ZrL complex.

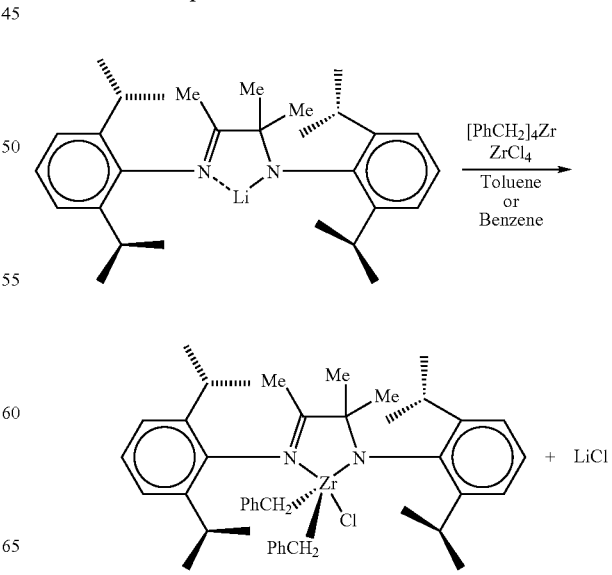

Synthesis of Bis(2,6-Dimethylphenyl)diazabutadiene

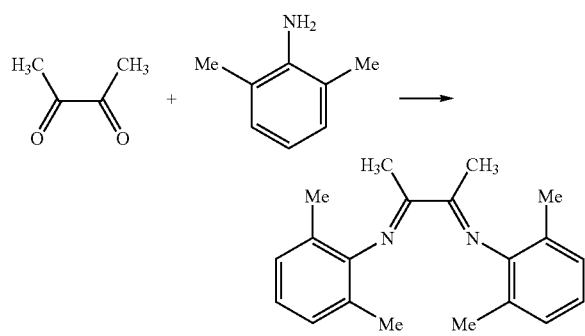

General procedure: 2,3-Butanedione (100 mmol, 8.6 g) was charged to a 100 mL Schlenk flask equipped with a stir bar and septum. Hydrochloric acid (5.0 mmol, 5.0 mL, [1.0M solution in ether]) was added with stirring under a nitrogen purge. 2,6-dimethylaniline (200 mmol, 24.2 g) was added. A Dean-Stark apparatus was attached and the reaction heated to 105° C. for 4 hrs and allowed to stir at room temperature overnight, then filtered and yellow solids were collected. The filtrate was allowed to stand overnight, then filtered a second crop of yellow solids was collected.

Alkylation of Bis (2,6-Dimethylphenyl)diazabutadiene

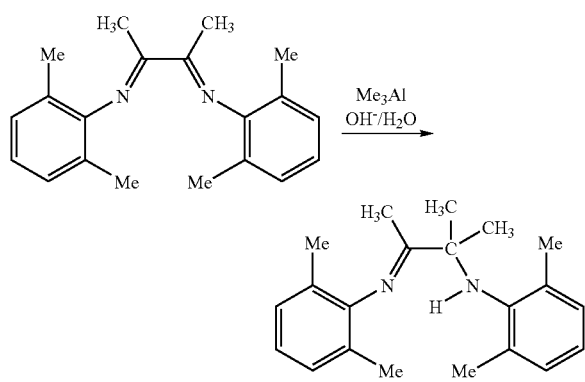

General procedure: Bis (2,6-Dimethylphenyl)diazabutadiene analogous to the monoalkylation of the diazabutadiene example, the above diazabutadiene compound (20 mmol, 5.8 g,) was dissolved in toluene (10 mL) in a 50 mL Schlenk flask equipped with a stir bar and septum. The reaction vessel was placed under a nitrogen purge and chilled to 0° C. Trimethyl aluminum (29 mmol, 18.1 mL, [2.0M solution in toluene]) was charged dropwise. The reaction was allowed to slowly warm to room temperature. The entire reaction solution was hydrolyzed by transferring into a stirring solution of sodium hydroxide and water and extracted with toluene. The extracts were dried over MgSO$_4$ then filtered. The filtrate was vacuum stripped to 4.8 g of red-orange liquid.

Reaction of Alkylated Bis (2,6-Dimethylphenyl)diazabutadiene with tetrakis(trimethylsilylmethyl)zirconium General procedure: Tetrakistrimethylsilylmethyl zirconium (0.100 mmol, 0.044 g) was charged to a 7 mL amber bottle equipped with a stir bar and cap. Alkylated bis (2,6-dimethylphenyl)diazabutadiene (0.100 mmol, 0.031 g) was charged to a second bottle. Benzene-d$_6$ (0.75 mL) was added to each bottle. The solution of 10-REMU-071 was transferred into the stirring solution of tetrakistrimethylsilylmethyl zirconium. The reaction solution was allowed to stir at room temperature overnight. Analysis by $^1$H NMR indicated very little reaction. Zirconium (IV) chloride (0.005 mmol, 0.001 g) was added to the reaction solution and allowed to stir overnight at room temperature.

Synthesis of 2,3-Butanedione (2,6-Diisopropylaniline) Mono-Imine

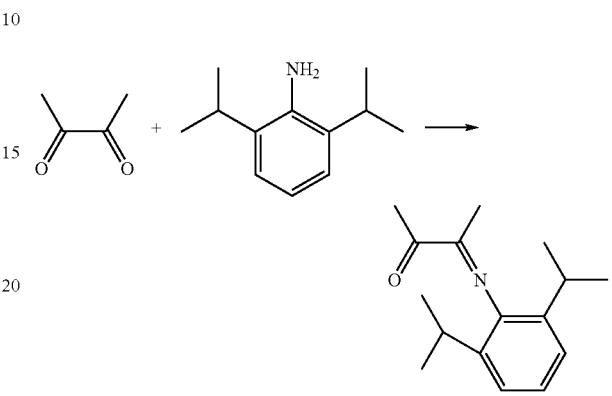

General procedure: 2,3-Butanedione (5000 mmol, 440 mL) was charged to a 3L flask equipped with a stir bar and septa. Hydrochloric acid (125 mL, [1.0M solution in ether]) was added with stirring. Methanol (1.0L) was added to dissolve. 2,6-Diisopropylaniline (2500 mmol, 470 mL) was added slowly into the stirring reaction. Reaction was allowed to stir at room temperature. When the reaction was complete a Vigreux fractional distillation head with a cold-water condenser was attached to the reaction flask and the reaction mixture distilled. The product was confirmed by $^1$H NMR in Benzene-d$_6$.

Cyclometallated Imino-Amide Catalyst Precursor

A novel cyclometallated imino-amide catalyst precursor; a nitrogen, nitrogen, carbon tridentate complex active in olefin polymerization is also part of the present invention. The structure is shown below to the right.

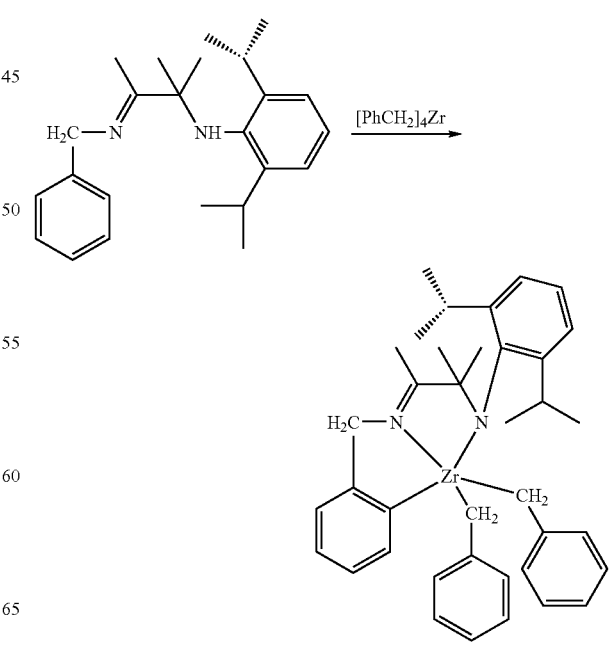

The reaction of benzyl-imine ligand was slow. Instead of the desired imino-amide zirconium tribenzyl complex, the product made the cyclometallated tridentate complex shown above. The imino-amide tribenzyl zirconiuims can cylcometallate to produce novel catalyst precursors that fit in the imino-amide category. The novel complex exhibited activity with modified methylaluminoxane cocatalyst.

MMAO Cocatalyst

| Run | Catalyst | $C_6$ mL | H2 psi | Activity |
|---|---|---|---|---|
| 6REMU12 | 5REMU77 | 43 | 0 | 2,824 |
| 6REMU35 | 5REMU77 | 43 | 5 | 5,647 |

Ene-Amide Catalyst Precursor

Novel ene-amide catalyst precursor complexes are also useful in olefin polymerizations according to the present invention. The zirconium ene-amide complex shown below was prepared by reacting the pyridyl imine ligand with [Me$_2$N]$_4$Zr. The value of such ene-amide complexes include application as catalysts and catalyst precursors. The double bond of the ene-amide also offers a synthon for creating a variety of new ligands and complexes for catalysts.

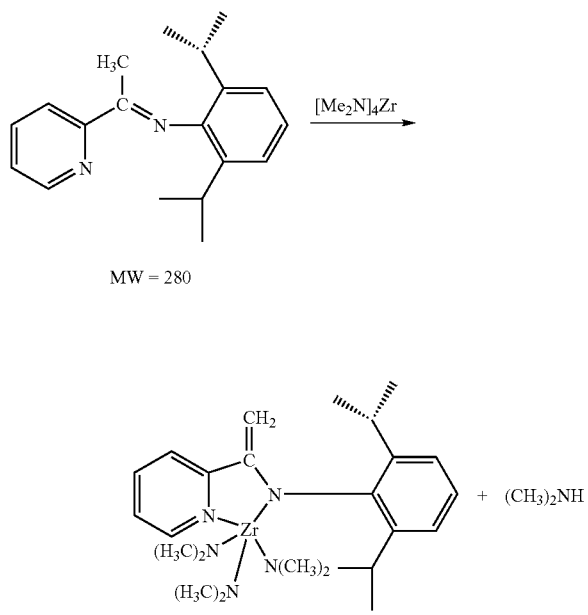

The novel complex exhibited activity with methylaluminoxane on silica (MOS) cocatalyst.

MOS Cocatalyst

| Co-cat mmoles | Temp. | Ethylene Press | P.E. Est.(g) | Activity |
|---|---|---|---|---|
| a. 0.150 | 85 | 85 | 6.1 | 8471 |
| b. 0.150 | 85 | 85 | 3.2 | 2824 |
| c. 0.150 | 85 | 85 | 7.9 | 14824 |

In Run a, the catalyst precursor was mixed w/10 equivalents of TMA for 5 minutes of contact before mixing w/MOS in toluene; 200 µmoles TIBA scavenger. In Run b, the catalyst precursor was mixed with 10 equivalents of TMA for 4 hours of contact before mixing with MOS in toluene; 200 µmoles TIBA scavenger. In Run c, the catalyst precursor was mixed with 1 equivalent of tetrabenzylzirconium to exchange dimethylamido ligands for benzyl ligands, mixed in toluene; 200 µmoles TIBA scavenger.

Run c was conducted in an effort to improve catalyst activity by exchanging the dimethylamido ligands on the trisamide ZrL precursor with benzyl ligands. The result indicates that activity is improved via this novel approach to benzyl exchange. The double bond of the ene-amide also offers a synthon for creating a variety of new ligands and complexes for catalysts.

Substituted Heterocyclic Imino-Amide Catalyst Precursor

The concept of a imino-amide catalyst precursor has been extended to include substituted heterocycle-containing derivatives of imino-amide complexes. While the examples herein will focus on pyridine derivatives, one of skill in the art will recognize that other heterocyclic moieties may be used. In the preferred embodiment, these complexes may comprise a nitrogen, nitrogen, carbon tridentate complex active useful in olefin polymerizations. In the preferred embodiment, the heterocycle is pyridine, such as the structure below.

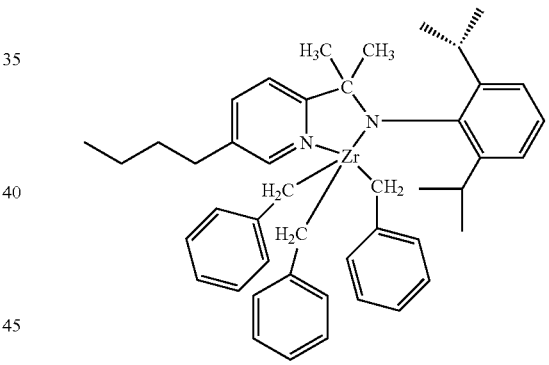

The realized benefit of this n-Butyl structural variation is greatly improved activity at low aluminoxane concentrations, which translates to low catalyst costs.

A synthetic route to a ligand possessing the general catalyst structure, but with a 5-n-butyl substituent on the pyridine ring is provided. One of skill in the art will recognize that other substitutions, both at other positions and with other groups is possible. The 5 n-butyl substitution apparently results from alkylation of the pyridine ring with n-butyllithium.

The benefit of this n-Butyl cyclometallated imino-amide structural variation was greatly improved activity at low aluminoxane concentrations, which translates to improved catalyst costs. In particular supported n-Butyl cyclometallated imino-amide systems for bimodal application is another use for this high molecular weight catalyst.

MMAO Cocatalyst, 0.5 micromoles Zr

| Run | Catalyst | MMAO/Zr | Activity | $I_2$ | $I_{21}$ | MFR | BBF IR |
|---|---|---|---|---|---|---|---|
| 1CCSX135 | 17REMU142 | 1,000 | 167,529 | 0.02 | 0.553 | 27.96 | 15.56 |
| 1CCSX137 | 17REMU142 | 300 | 168,471 | 0.013 | 0.589 | 46.54 | 11.49 |
| 1CCSX139 | 17REMU142 | 150 | 129,412 | NF | 0.262 | NF | 7.25 |

Conditions: 85° C., 85 psi ethylene, 43 mL hexene, no hydrogen.

MMAO Cocatalyst, 0.25 micromoles Zr

| Run | Catalyst | MMAO/Zr | Activity | $I_2$ | $I_{21}$ | MFR | BBF IR |
|---|---|---|---|---|---|---|---|
| 1CCSX141 | 17REMU142 | 300 | 240,000 | NF | 0.092 | NF | 7.29 |
| 1CCSX143 | 17REMU142 | 150 | 112,941 | 0.016 | 0.765 | 49.04 | 7.82 |

Conditions: 85° C., 85 psi ethylene, 43 mL hexene, no hydrogen.

MAO on Silica 4.5 mmoles Al/gram Cocatalyst, 1.0 micromoles Zr (Toluene Solvent)

| Run | Catalyst | MOS/Zr | Activity | $I_2$ | $I_{21}$ | MFR | BBF IR |
|---|---|---|---|---|---|---|---|
| 1CCSX145 | 17REMU142 | 300 | 112,706 | NF | NF | NF | 7.62 |
| 1CCSX147 | 17REMU142 | 160 | 77,647 | — | — | — | 7.83 |

Conditions: 85° C., 85 psi ethylene, 43 mL hexene, no hydrogen.

Using commercially available 4-methyl-2-acetylpyridine, the 4-methyl cyclometallated imino-amide according to the reaction scheme shown below.

Polymerization evaluations of these complexes with modified methylaluminoxane (MMAO) both demonstrated good polymerization activity at low MMAO/Zr ratios (MMAO/Zr=150, 200 eq TIBA scavenger).

4-Methylpyridyl Cyclometallated Imino-Amide/MMAO Polymerizations:

MMAO Cocatalyst, 0.5 micromoles Zr

| Run | Catalyst | MMAO/Zr | Activity | $I_2$ | $I_{21}$ | MFR | BBF IR |
|---|---|---|---|---|---|---|---|
| 2CCSX75 | 18REMU11 | 1,000 | 170,824 | NF | NF | NF | 10.15 |
| 2CCSX81 | 18REMU11 | 150 | 105,412 | — | — | — | 8.0 |

Conditions: 85° C., 85 psi ethylene, 43 mL hexene, no hydrogen.

The activity for this analog (carbonmethylbenzyl bridge) was encouraging, especially at low Al/Zr ratios.

4-Methylpyridyl Cyclometallated Imino-Amide/MMAO Polymerizations

| | | MMAO Cocatalyst, 0.5 micromoles Zr | | | | | |
|---|---|---|---|---|---|---|---|
| Run | Catalyst | MMAO/Zr | Activity | I₂ | I₂₁ | MFR | BBF IR |
| 2CCSX77 | 18REMU13 | 1,000 | 214,118 | — | — | — | 12.69 |
| 2CCSX83 | 18REMU13 | 150 | 175,529 | — | — | — | 12.01 |

Conditions: 85° C., 85 psi ethylene, 43 mL hexene, no hydrogen.

The activity of this analog (carbondimethyl bridge) was also elevated, especially at the low Al/Zr ratio. The conclusion is that pyridne alkylation in the 4 or 5 positions for Q catalyst appears to improve low Al/Zr activity.

What is claimed is:

1. A catalyst precursor represented by:

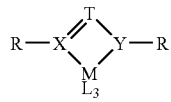

wherein T is a bridging group containing 2 or more bridging atoms;
M is zirconium or hafnium,
each L is a monovalent anionic ligand;
X is nitrogen;
Y is nitrogen; and,
wherein each R is the same or different and is a bulky substituent that is sterically hindering with respect to X and Y.

2. The catalyst precursor of claim 1, wherein T contains 2 or 3 bridging atoms and contains from 2 to 50 non-hydrogen atoms, at least one of which is a Group 14 atom.

3. The catalyst precursor of claim 1, wherein T contains at least two primary alkyl groups on the atom adjacent to Y.

4. The catalyst precursor of claim 1, wherein T contains a two methyl groups on the atom adjacent to Y.

5. The catalyst precursor of claim 1, wherein T is selected from the group consisting of:

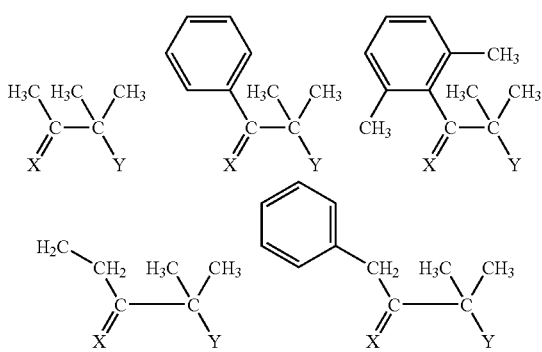

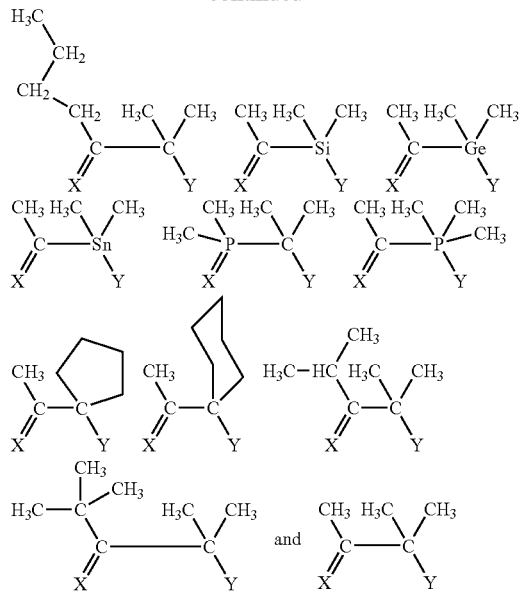

wherein X and Y are provided for convenience and are not part of the bridging group.

6. The catalyst precursor of claim 1, wherein R is a substituted heterocylic ring, said substituted heterocyclic ring including one of X and Y, or both X and Y, as a heteroatom.

7. The catalyst precursor of claim 1, wherein each L group contains from 1 to 50 non-hydrogen atoms and is selected from the group consisting of halogen containing groups, alkyl, aryl, alkenyl, alkylaryl, arylalkyl, hydrocarboxy, amides, phosphides, sulfides, silylalkyls, diketones, borohydrides, and carboxylates.

8. The catalyst precursor of claim 1, wherein L contains from 1 to 20 non-hydrogen atoms and is selected from the group consisting of alkyl, arylalkyl, and halogen.

9. The catalyst precursor of claim 6, wherein said substituted heterocyclic ring is 5-n-butyl pyridine.

10. The catalyst precursor of claim 6, wherein said substituted heterocyclic ring is 4-methyl pyridine.

11. The catalyst precursor of claim 1, wherein R contains from 3 to 50 non-hydrogen atoms and is an alkyl, alkenyl, cycloalkyl, heterocyclic, alkylaryl, arylalkyl, polymeric or inorganic ring moiety.

12. The catalyst precursor of claim 11, wherein R contains from 4 to 20 non-hydrogen atoms.

13. The catalyst precursor of claim 11, a wherein R has one or more of its carbon or hydrogen positions substituted with an element selected from Groups 14 to 17 of the Periodic Table of the Elements, other than carbon.

14. The catalyst precursor of claim 1, having the following formula

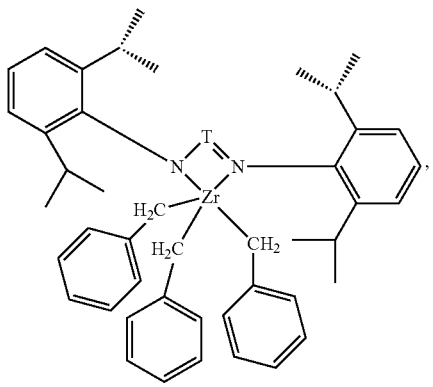

wherein T is a bridging group containing 2 or more bridging atoms.

15. The catalyst precursor of claim 1, which is represented by a formula selected from the group consisting of:

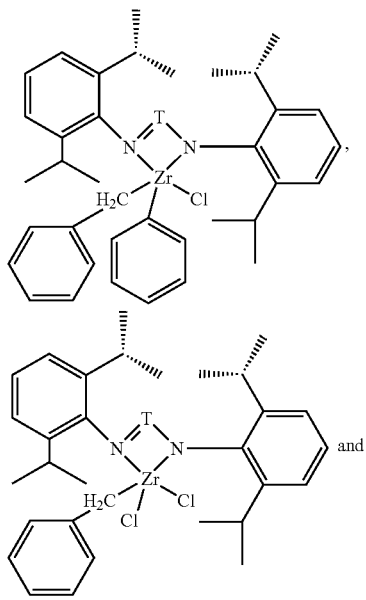

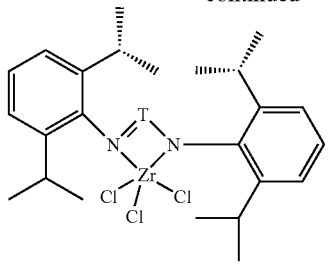

wherein T is a bridging group containing 2 or more bridging atoms.

16. The catalyst precursor of claim 6, having the following structure:

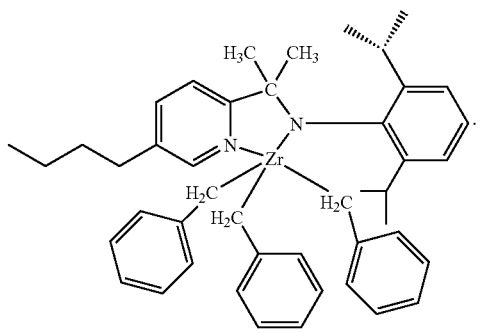

17. The catalyst precursor of claim 6 having the following structure:

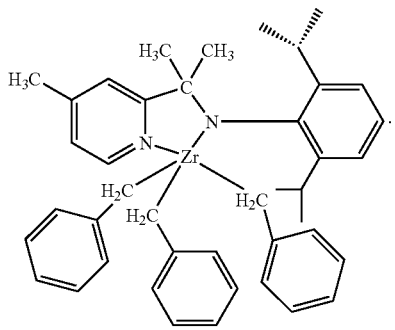

* * * * *